(12) United States Patent
Peng et al.

(10) Patent No.: US 9,026,404 B2
(45) Date of Patent: May 5, 2015

(54) METHODS OF IMPROVING DETECTORS AND CLASSIFIERS USING OPTIMIZED STOCHASTIC RESONANCE NOISE

(75) Inventors: Renbin Peng, San Jose, CA (US); Pramod K. Varshney, Fayetteville, NY (US)

(73) Assignee: Syracuse University, Syracuse, NY (US)

( * ) Notice: Subject to any disclaimer, the term of this patent is extended or adjusted under 35 U.S.C. 154(b) by 631 days.

(21) Appl. No.: 13/410,949

(22) Filed: Mar. 2, 2012

(65) Prior Publication Data

US 2012/0278039 A1 Nov. 1, 2012

Related U.S. Application Data

(63) Continuation-in-part of application No. 12/710,143, filed on Feb. 22, 2010, now Pat. No. 8,214,177, which is a continuation-in-part of application No. 11/551,473, filed on Oct. 20, 2006, now Pat. No. 7,668,699.

(60) Provisional application No. 60/728,504, filed on Oct. 20, 2005.

(51) Int. Cl.
*H04B 15/00* (2006.01)
*A61B 6/00* (2006.01)
*G06T 5/20* (2006.01)
(Continued)

(52) U.S. Cl.
CPC . *A61B 6/502* (2013.01); *G06T 5/20* (2013.01); *G06T 2207/10116* (2013.01); *G06T 2207/30068* (2013.01); *H04B 17/007* (2013.01); *G06T 5/002* (2013.01)

(58) Field of Classification Search
CPC .............................. H04B 17/007; A61B 6/502
USPC ........................................ 702/179–181, 191
See application file for complete search history.

(56) References Cited

U.S. PATENT DOCUMENTS 6,137,898 A * 10/2000 Broussard et al. ............ 382/132
2002/0181797 A1* 12/2002 Young ........................... 382/260
(Continued)

OTHER PUBLICATIONS

Chan, et al., "Improvement in radiologist's detection of clustered micro-calcifications on mammograms," Investigative Radiol. vol. 25, pp. 1102-1110, 1990.
(Continued)

*Primary Examiner* — Phuong Huynh
(74) *Attorney, Agent, or Firm* — Frederick J. M. Price; David L. Nocilly; Bond Schoeneck & King, PLLC

(57) ABSTRACT

Apparatus and method for improving the performance of a threshold-based detector or classifier, or a generic detector or classifier and increasing the probability of detecting at least one object in an image using novel algorithms and stochastic resonance noise is provided, where a suitable dose of noise is introduced to the image data such that the performance of the above-referenced detectors or classifiers is improved without altering the detector's or classifier's parameters. Several stochastic resonance (SR) noise-based detection and classification enhancement schemes are presented. The SR noise-enhanced detection and classification schemes can improve any algorithms and systems. To implement these schemes, the only knowledge that is needed is the original input data (no matter 1D, 2D, 3D or others) and the output (detection results) of the existing algorithms and systems.

23 Claims, 14 Drawing Sheets

(51) Int. Cl.
*H04B 17/00* (2006.01)
*G06T 5/00* (2006.01)
*G06F 19/00* (2011.01)

(56) References Cited

U.S. PATENT DOCUMENTS

2006/0020452 A1  1/2006  Nakatani et al.
2006/0052828 A1*  3/2006  Kim et al. .................... 607/3
2006/0074558 A1  4/2006  Williamson et al.

OTHER PUBLICATIONS

Astley, et al., "Automation in mammography: Computer vision and human perception," Int. J. Pattern Recognition Artificial Intell., vol. 7, No. 6, pp. 1313-1338, 1993.
Bazzani et al., "Automatic detection of clustered micro-calcifications in digital mammograms using an SVM classifier," in Proc. of European Symposium on Artificial Neural Networks Plastics, Bruges, Apr. 26-28, 2000.
Gurcan, et al., "Influence function based gaussianity tests for detection of micro-calcifications in mammogram images," in Proc. International Conference on Image Processing (ICIP), vol. 3, pp. 407-411, 1999.
Karssemeijer, "Adaptive noise equalization and recognition of micro-calcification clusters in mammograms," Int. J. Pattern Recognit. Artificial Intell., vol. 7, No. 6, pp. 1357-1376, 1993.
Nakayaman, et al. "Computer-aided diagnosis scheme using a filter bank for detection of micro-calcification clusters in mammograms," IEEE Trans. on Biomedical Engineering, vol. 53, No. 2, pp. 273-283, Feb. 2006.
Regentova, et al., "Detecting micro-calcifications in digital mammograms using wavelet domain hidden markov tree model," in Proc. 28th Annual International Conference of the IEEE Engineering in Medicine and Biology Society 2006 (EMBS '06), pp. 1972-1975, Aug. 30-Sep. 3, 2006.
Deepa et al., "Fractal modeling of mammograms based on mean and variance for the detection of microcalcifications," in Proc. International Conference on Computational Intelligence and Multimedia Applications, vol. 2, pp. 334-348, Dec. 13-15, 2007.
Wei et al., "Relevance vector machine for automatic detection of clustered micro-calcifications," IEEE Trans. on Medical Imaging, vol. 24, No. 10, pp. 1278-1285, Oct. 2005.
Catanzariti, et al. "A CAD system for the detection of mammographyc micro-calcifications based on Gabor Transform," in Proc. Nuclear Science Symposium Conference Record, vol. 6, pp. 3599-3603, Oct. 16-22, 2004.
Strickland, et al., "Wavelet transform for detecting micro-calcifications in mammograms," IEEE Trans. Med. Imag., vol. 15, pp. 218-299, Apr. 1996.
Strickland, R.N. , "Wavelet transform methods for objects detection and recovery," IEEE Trans. Image Processing, vol. 6, pp. 724-735, May 1997.
Lemaur, et al., Highly regular wavelets for the detection of clustered micro-calcifications in mammograms, IEEE Trans. on Medical Imaging, vol. 22, No. 3, Mar. 2003.
Kai-Yang Li, et al., "A novel method of detecting calcifications from mammogram images based on wavelet and sobel detector," in Proc. 2006 IEEE International Conference on Mechatronics and Automation, pp. 1503-1508, Jun. 2006.
Stein et al., "Anomaly detection from hyperspectral imagery," IEEE Signal Processing Magazine, vol. 19, pp. 58-69, Jan. 2002.
Benzi, et al., "The mechanism of stochastic resonance," Journal of Physics A: Mathematical and General, vol. 14, pp. L453-L457, 1981.
Kay, Steven, "Can Detectability Be Improved by Adding Noise?" IEEE Signal Processing Letters, vol. 7, No. 1, pp. 8-10, Jan. 2000.
Gammaitoni, et al., "Stochastic resonance," Rev. Mod. Phys. vol. 70, No. 1, pp. 223-287, Jan. 1998.
Loerincz et al, "A stochastic resonator is able to greatly improve signal-to-noise ratio," Physics Letters A, vol, 224, pp. 63-67, 1996.
Bezrukov, et al, "Stochastic resonance in non-dynamical systems without response thresholds," Nature, vol. 385, pp. 319-321, Jan. 1997.
Chen, et al., "Theory of the stochastic resonance effect in signal detection: Part 1—fixed detectors," IEEE Transaction on Signal Processing, vol. 55, No. 7, pp. 3172-3184, Jul. 2007.
Chen, et al., "Theory of the stochastic resonance effect in signal detection: Part II—variable detectors," to appear in IEEE Transaction on Signal Processing, 2008.
Devijver, et al., Pattern Recognition: A Statistical Approach, Prentice Hall, Englewood Cliffs, London, 1982.
Available: http://peipa.essex.ac.uk/info/mias.html.
Available: http://marathon.csee.usf.edu/Mammography/Database.html.
Gurcan et al., "2-D adaptive prediction based Gaussianity tests in micro-calcification detection," Proceedings of SPIE, Visual Communications and Image Processing, vol. 3309, 1997.
Kay, Steven M., Fundamentals of Statistical Signal Processing-Detection Theory, Prentice Hall PTR (1998.
Sezgin, et al., "Survey over image thresholding techniques and quantitative performance evaluation," Journal of Electronic Imaging, 13(1), pp. 146-165, Jan. 2004.
Lin et al., "Two-dimensional LMS adaptive filter incorporating a local-mean estimator for image processing," IEEE Trans. on Circuits and Systems—11: Analog and digital signal processing, vol. 40, No. 1, Jul. 1993.
Rank, et al., "Estimation of image noise variance," IEE Proc.—Vis. Image Signal Process, vol., 146 No. 2, Apr. 1999.
Poor, H. Vincent, An Introduction to Signal Detection and Estimation (second edition) Springer, 1994.
Kolata, Gina, "Study questions computerized breast cancer detection," The New York Times National, Thur., Apr. 5, 2007.
Banerje et al., "Tumor detection in digital mammograms," in Proc. International Conference on Image Processing (ICIP '00), vol. 3, pp. 432-435, Vancouver, BC, Canada 2000.
Nikias et al., Signal Processing with Alpha-Stable Distributions and Applications, John Wiley and Sons, Inc. 1995.
Kay et al., "Reducing probability of error using stochastic resonance," IEEE Signal Processing Letters, vol. 13, No. 11, pp. 695-298, Nov. 2006.
Fukunaga, Kinosuke, Introduction to Statistical Pattern Recognition (second edition), Academic Press, Sep. 1990.
Efron et al., An Introduction to the Bootstrap, Chapman & Hall, 1993.
De La Rosa et al., "Boostrap Methods for a Measurement Estimation Problem," IEEE Trans. Instrumentation and Measurement, vol. 55, No. 3, pp. 820-827, Jun. 2006.
Kittler, et al., "Minimum error thresholds," Pattern Recognition, vol. 19., No. 1, pp. 41-47, 1986 40.
Diyana, et al., "A comparison of clustered micro-calcifications automated detection methods in digital mammogram," in Proc. International Conference on Acoustics, Speech, and Signal Processing (ICASSP), vol. 2, pp. 11-385-8 6-10, Apr. 2003.
Mclachlan and Peel, Finite Mixture Models, Sections 2.8 to 2.12, A Wiley-Interscience Publication, Oct. 2, 2000.
Cheng, et al, "A novel approach to micro-calcification detection using fuzzy logic technique," IEEE Trans. on Medical Imaging, vol. 17, No. 3, Jun. 1998.

* cited by examiner

METHODS OF IMPROVING DETECTORS AND CLASSIFIERS USING OPTIMIZED STOCHASTIC RESONANCE NOISE

CROSS-REFERENCE TO RELATED APPLICATIONS

This application claims priority U.S. application Ser. No. 12/710,143, filed on Feb. 22, 2010, which claims priority to U.S. application Ser. No. 11/551,473, filed on Oct. 20, 2006 (now U.S. patent application Ser. No. 7,668,699), which claims priority to U.S. Provisional Patent Application No. 60/728,504, filed on Oct. 20, 2005, each of which are incorporated by reference herein in their respective entireties.

STATEMENT REGARDING FEDERALLY SPONSORED RESEARCH OR DEVELOPMENT

This invention was made with government support under Grant No. FA9550-09-1-0064, which was awarded by the Air Force Office of Scientific Research (AFOSR). The government has certain rights in the invention.

BACKGROUND OF THE INVENTION

1. Field of the Invention

The present invention relates to detection and classification, and more particularly, to a method for detecting objects in an image (such as lesions in a mammogram image), and aims at improving thresholding-based detectors and classifiers as well as general detectors and classifiers using novel algorithms and stochastic resonance noise 2. Description of the Related Art Stochastic resonance (SR) is a nonlinear physical phenomenon in which the output signals of some nonlinear systems can be enhanced by adding suitable noise under certain conditions. The classic SR signature is the signal-to-noise ratio (SNR) gain of certain nonlinear systems, i.e., the output SNR is higher than the input SNR when an appropriate amount of noise is added.

Although SNR is a very important measure of system performance, SNR gain-based SR approaches have several limitations. First, the definition of SNR is not uniform and it varies from one application to another. Second, to optimize the performance, the complete a priori knowledge of the signal is required. Finally, for detection problems where the noise is non-Gaussian, SNR is not always directly related to detection performance; i.e., optimizing output SNR does not guarantee optimizing probability of detection.

In signal detection theory, SR also plays a very important role in improving the signal detectability. For example, improvement of detection performance of a weak sinusoid signal has been reported. To detect a DC signal in a Gaussian mixture noise background, performance of the sign detector can be enhanced by adding some white Gaussian noise under certain circumstances. For the suboptimal detector known as the locally optimal detector (LOD), detection performance is optimum when the noise parameters and detector parameters are matched. The stochastic resonance phenomenon in quantizers results in a better detection performance can be achieved by a proper choice of the quantizer thresholds. Detection performance can be further improved by using an optimal detector on the output signal. Despite the progress achieved by the above approaches, the use the SR effect in signal detection systems is rather limited and does not fully consider the underlying theory of SR.

Simple and robust suboptimal detectors are used in numerous applications. To improve a suboptimal detector detection performance, two approaches are widely used. In the first approach, the detector parameters are varied. Alternatively, when the detector itself cannot be altered or the optimum parameter values are difficult to obtain, adjusting the observed data becomes a viable approach. Adding a dependent noise is not always possible because pertinent prior information is usually not available.

For some suboptimal detectors, detection performance can be improved by adding an independent noise to the data under certain conditions. For a given type of SR noise, the optimal amount of noise can be determined that maximizes the detection performance for a given suboptimal detector. However, despite the progress made, the underlying mechanism of the SR phenomenon as it relates to detection problems has not fully been explored. For example, until now the "best" noise to be added in order to achieve the best achievable detection performance for the suboptimal detector was not known. Additionally, the optimal level of noise that should be used for enhanced performance was also unknown.

Breast cancer is a serious disease with high occurrence rate in women. There is clear evidence which shows that early diagnosis and treatment of breast cancer can significantly increase the chance of survival for patients. One of the important early symptoms of breast cancer in the mammograms is the appearance of micro-calcification clusters. An accurate detection of micro-calcifications is highly desirable to ensure early diagnosis of breast cancer.

Automatic micro-calcification detection techniques play an important role in cancer diagnosis and treatment. This, however, still remains a challenging task.

For example, computer-aided diagnosis (CAD) improves the diagnostic performance of radiologists and is an effective method for early diagnosis thereby increasing survival time for women with breast cancer. While advances have been made in the area of CAD for digital mammograms, the main challenge of accurately identifying breast cancer in digital mammograms still remains, which is due to the small sizes and subtle contrast of the lesions compared with the surrounding normal breast tissues.

Much effort has been made for detecting micro-calcifications by using CAD techniques. Some methods tried to detect micro-calcifications through a modeling procedure. For example, Bazzani et al. and Gurcan et al. detected the micro-calcifications by using Gaussianity tests in the difference and filtered mammograms, respectively. See Armando Bazzani et al., "Automatic detection of clustered micro-calcifications in digital mammograms using an SVM classifier," in Proc. of European Symposium on Artificial Neural Networks Plastics, Bruges, 26-28 Apr. 2000; M. Nafi Gurcan, Yasemin Yardimci, and A. Enis Getin, "Influence function based gaussianity tests for detection of micro-calcifications in mammogram images," in Proc. International Conference on Image Processing (ICIP), vol. 3, pp. 407-411, 1999. Karssemeijer modeled the mammograms using Markov random fields. See N. Karssemeijer, "Adaptive noise equalization and recognition of micro-calcification clusters in mammograms," Int. J. Pattern Recognit. Artificial Intell., vol. 7, no. 6, pp. 1357-1376, 1993. Nakayama et al. used a Gaussian probability density function (pdf) to model the abnormal regions in the subband mammograms generated by a novel filter bank. See Ryohei Nakayama et al, "Computer-aided diagnosis scheme using a filter bank for detection of micro-calcification clusters in mammograms;" IEEE Trans. on Biomedical Engineering, vol. 53, no. 2, pp. 273-283, February 2006. Regentova et al. considered the pdf of the magnitudes of the wavelet coefficients, which are assumed to correspond to two hidden Markov states, to obey zero mean Gaussian distributions with different variances. See Emma Regentova et al, "Detecting micro-calcifications in digital mammograms using wavelet domain hidden markov tree model," in Proc. 28th Annual International Conference of the IEEE Engineering in Medicine and Biology Society 2006 (EMBS '06), pp. 1972-1975, 30 Aug.-3 Sep. 2006.

Deepa and Tessamma used the deterministic fractal model to characterize breast background tissues. See Sankar Deepa and Thomas Tessamma, "Fractal modeling of mammograms based on mean and variance for the detection of micro-calcifications," in Proc. International Conference on Computational Intelligence and Multimedia Applications, vol. 2, pp. 334-348, 13-15 Dec. 2007. The challenge for these model-based methods is that an accurate model is generally not easy to obtain and model mismatch is hard to avoid, so the detection results are deteriorated. There are also some methods that attempt to avoid the necessity of modeling during the detection process. For example, in Wei et al., relevance vector machine (RVM) was employed as a micro-calcification classifier, and its parameters were determined through a supervised learning procedure. See Liyang Wei et al., "Relevance vector machine for automatic detection of clustered micro-calcifications," IEEE Trans. on Medical Imaging, vol. 24, no. 10, pp. 1278-1285, October 2005. Catanzariti et al. trained a three-layer feed-forward artificial neural network (ANN) to detect micro-calcifications using the features extracted by a bank of Gabor filters. See Catanzariti et al, "A CAD system for the detection of mammographyc micro-calcifications based on Gabor Transform," in Proc. Nuclear Science Symposium Conference Record, vol. 6, pp. 3599-3603, 16-22 Oct. 2004.

Strickland et al., Lemaur et al. and Li and Dong proposed the wavelet domain thresholding techniques to obtain the information of interest for the detection of micro-calcifications. See R. N. Strickland, "Wavelet transform methods for objects detection and recovery," IEEE Trans. Image Processing, vol. 6, pp. 724-735, May, 1997; G. Lemaur, K. Drouiche, and J. DeConinck, "Highly regular wavelets for the detection of clustered micro-calcifications in mammograms," IEEE Trans. on Medical Imaging, vol. 22, no. 3, March, 2003; Kai-yang Li and Zheng Dong, "A novel method of detecting calcifications from mammogram images based on wavelet and sobel detector," in Proc. 2006 IEEE International Conference on Mechatronics and Automation, pp. 1503-1508, June 2006. These methods partially bypassed the modeling problems, but determination of the optimum parameters, such as the threshold, is still a very challenging task, and the detection performance was often affected by the suboptimum parameters. Basically, lesion detection can be considered as an anomaly detection problem. Performance of the detectors is heavily dependent on the accuracy of the mathematical models and the detector parameters. However, appropriate models and optimum parameter values are generally very difficult to obtain in practical applications, which often results in unsatisfactory detection performance in terms of high probability of false alarm ($P_F$) and low probability of detection ($P_D$).

Description Of the Related Art Section Disclaimer: To the extent that specific publications are discussed above in this Description of the Related Art Section, or elsewhere herein, these discussions should not be taken as an admission that the discussed publications (for example, technical/scientific publications) are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section, or elsewhere herein, they are all hereby incorporated by reference into this document in their respective entirety(ies).

BRIEF SUMMARY OF THE INVENTION

It is therefore a principal object and advantage of the present invention to provide a method for determining the best noise to add to improve detection of a suboptimal, non-linear detector.

It is an additional object and advantage of the present invention to provide a method for determining the optimal level of noise for improved detection.

In accordance with the foregoing objects and advantages, the present invention provides a method for signal detection in observed sensor data for a broad range of electromagnetic or acoustic applications such as radar, sonar, as well as imagery such as visual, hyperspectral, and multi-spectral. The method of the present invention is applicable in applications involving non-linear processing of the data. Specifically, the method of the present invention determines the stochastic resonance noise probability density function to be added to either the observed data process to optimize detection with no increase in the false alarm rate, or to an image to optimize the detection of signal objects from the background. In addition, the method of the present invention determines the conditions required for performance improvement using additive stochastic resonance noise. The method of the present invention also yields a constant false alarm rate (CFAR) receiver implementation, which is essential in operational conditions in which it is imperative to maintain false alarm rates without adjusting the detector threshold level.

In accordance with an additional embodiment of the present invention, an apparatus and method for detecting micro-calcifications in mammograms using novel algorithms and stochastic resonance noise is provided, where a suitable dose of noise is added to the abnormal mammograms such that the performance of a suboptimal lesion detector is improved without altering the detector's parameters. As discussed further below in the Detailed Description of the Invention section, a stochastic resonance noise-based detection approach is presented to improve some suboptimal detectors which suffer from model mismatch due to the Gaussian assumption. Furthermore, a stochastic resonance noise-based detection enhancement framework is presented to deal with more general model mismatch cases. The algorithms and the framework are tested on a set of 75 representative abnormal mammograms. The results show that they yield superior performance when compared with several other classification and detection approaches.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 1:
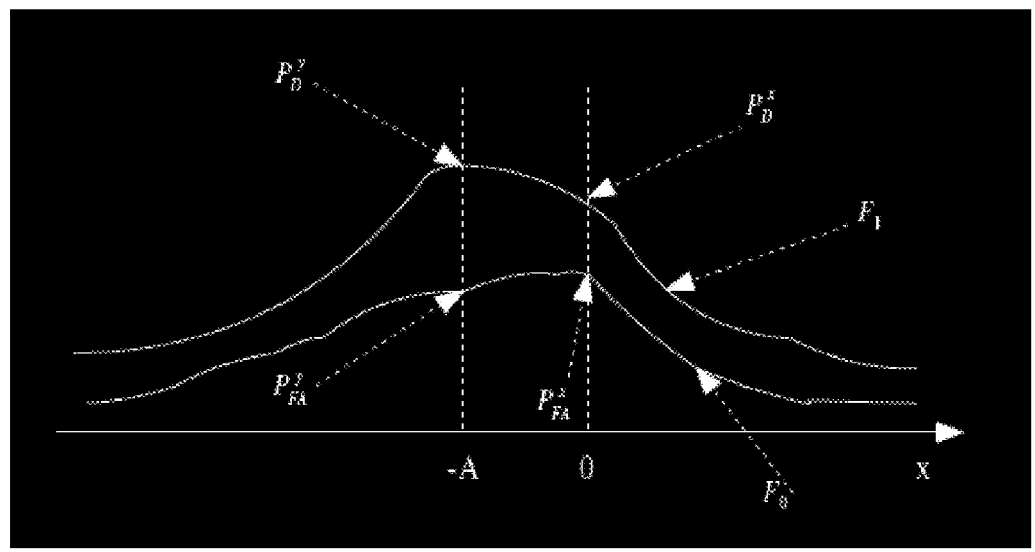
FIG. 1 is a graph of the effect of additive noise according to the present invention.

Referring now to the drawings, wherein like reference numerals refer to like parts throughout, there is seen in FIG. 1 a chart illustrating the effective of additive noise on a given signal.

The following definitions serve to clarify the present invention:

The term "constant false alarm rate" (CFAR) refers to the attribute of a receiver that maintains the false alarm rate fixed in the presence of changing interference levels.

The term "false alarm" refers to the decision that a signal is present when in fact it is not.

The term "false alarm rate" refers to the rate at which a false alarm occurs.

The term "fixed detector" refers to a detector comprised of a fixed test statistic and a fixed threshold. The term "receiver operating characteristic" (ROC) refers to a plot of the probability of detection as a function of the probability of false alarm for a given detector. To enhance the detection performance, noise is added to an original data process x to obtain a new data process y given by y=x+n, where n is either an independent random process with pdf $p_n(\cdot)$ or a nonrandom signal. There is no constraint on n. For example, n can be white noise, colored noise, or even be a deterministic signal A, corresponding to $p_n(n)=\delta(n-A)$. As described herein, depending on the detection problem, an improvement of detection performance may not always be possible. In that case, the optimal noise is equal to zero. The pdf of y is expressed by the convolutions of the pdfs such that $$p_y(y)=p_x(x)*p_n(x)=\int_{R^N} p_x(x)p_n(y-n)dx) \quad (7)$$

The binary hypotheses testing problem for this new observed data y can be expressed as:

$$\begin{cases} H_0: \ p_y(y; H_0) = \int_{R^N} p_0(x)p_n(y-x)\,dx \\ H_1: \ p_y(y; H_1) = \int_{R^N} p_1(x)p_n(y-x)\,dx \end{cases} \quad (8)$$

Since the detector is fixed, i.e., the critical function φ of y is the same as that for x, the probability of detection based on data y is given by, $$\begin{aligned} P_D^y &= \int_{R^N} \phi(y) p_y(y; H_1)\,dy \\ &= \int_{R^N} \phi(y) \int_{R^N} p_1(x) p_n(y-x)\,dx\,dy \\ &= \int_{R^N} p_1(x)\left(\int_{R^N} \phi(y) p_n(y-x)\,dy\right)dx \\ &= \int_{R^N} p_1(x) C_{n,\phi}(x)\,dx \\ &= E_1[C_{n,\phi}(x)]) \end{aligned} \quad (9)$$

Where $$C_{n,\phi}(x)=\int_{R^N} \phi(y) p_n(y-x)\,dy \quad (10)$$

Alternatively, $$\begin{aligned} P_D^y &= \int_{R^N} p_n(x)\left(\int_{R^N} \phi(y) p_1(y-x)\,dy\right)dx \\ &= F_{1,\phi}(x) p_n(x)\,dx \\ &= E_n(F_{1,\phi}(x)) \end{aligned} \quad (11)$$

Similarly, $$\begin{aligned} P_{FA}^y &= \int_{R^N} p_0(x) C_{n,\phi}(x)\,dx \\ &= E_0[C_{n,\phi}(x)] \\ &= \int F_{0,\phi}(x) p_n(x)\,dx \\ &= E_n(F_{0,\phi}(x)) \end{aligned} \quad (12)(13)$$

where $$F_{i,\phi}(x)=\int_{R^N}\phi(y)p_i(y-x)dy \ i=0, 1, \quad (14)$$

corresponding to hypothesis $H_i$. $E_i(\cdot)$, $E_n(\cdot)$ are the expected values based on distributions $p_i$ and $p_n$, respectively, and $P_{FA}^x=F_{0,\phi}(0)$, $P_D^x=F_{1,\phi}(0)$. To simplify notation, subscript φ of F and C may be omitted and denotes as $F_1$, $F_0$, and $C_n$, respectively. Further, $F_1(x_0)$ and $F_0(x_0)$ are actually the probability of detection and probability of false alarm, respectively, for this detection scheme with input $y=x+x_0$. For example, $F_1(-2)$ is the $P_D$ of this detection scheme with input x-2. Therefore, it is very convenient to obtain the $F_1$ and $F_0$ values by analytical computation if $p_0$, $p_1$ and φ are known. When they are not available, $F_1$ and $F_0$ can be obtained from the data itself by processing it through the detector and recording the detection performance. The optimal SR noise definition may be formalized as follows.

Consider the two hypotheses detection problem. The pdf of optimum SR noise is given by $$p_n^{opt} = \operatorname*{argmax}_{p_n} \int_{R^N} F_1(x) p_n(x) dx \qquad (15)$$

where $p_n(x) \geq 0, x \in R^N.$  1)

$\int_{R^N} p_n(x) dx = 1.$  2)

$\int_{R^N} F_0(x) p_n(x) dx \leq F_0(0).$  3)

Conditions 1) and 2) are fundamental properties of a pdf function. Condition 3) ensures that $P^y_{FA} \leq P^x_{FA}$, i.e., the $P_{FA}$ constraint specified under the Neyman-Pearson Criterion is satisfied. Further, if the inequality of condition 3) becomes equality, the Constant False Alarm Rate (CFAR) property of the original detector is maintained. A simple illustration of the effect of additive noise is shown in FIG. 1. In the example, $$F_1(-A) = \max_x F_1(x) \text{ and } F_0(-A) < F_0(0),$$

hence $p_n^{opt} = \delta(x+A)$ which means the optimal SR noise $n = -A$ is a dc signal with value $-A$. In practical applications, some additional restrictions on the noise may also be applied. For example, the type of noise may be restricted, (e.g., n may be specified as Gaussian noise), or we may require a noise with even symmetric pdf $p_n(x) = p_n(-x)$ to ensure that the mean value of y is equal to the mean value of x. However, regardless of the additional restrictions, the conditions 1), 2), and 3) are always valid and the optimum noise pdf can be determined for these conditions.

In general, for optimum SR noise detection in Neyman-Peason detection, it is difficult to find the exact form of $p_n(\cdot)$ directly because of condition 3). However, an alternative approach considers the relationship between $p_n(x)$ and $F_i(x)$. From equation (14), for a given value $f_0$ of $F_0$, we have $x = F_0^{-1}(f_0)$, where $F_0^{-1}$ is the inverse function of $F_0$. When $F_0$ is a one-to-one mapping function, x is a unique vector. Otherwise, $F_0^{-1}(f_0)$ is a set of x for which $F_0(x) = f_0$. Therefore, we can express a value or a set of values $f_1$ of $F_1$ as $f_1 = F_1(x) = F_1(F_0^{-1}(f_0))$  (16)

Given the noise distribution of $p_n(\cdot)$ in the original RN domain, $p_{n,f_0}(\cdot)$ the noise distribution in the $f_0$ domain can also be uniquely determined. Further, the conditions on the optimum noise can be rewritten in terms of $f_0$ equivalently as $p_{n,f_0}(f_0) \geq 0$  4)

$\int p_{n,f_0}(f_0) df_0 = 1$  5)

$\int f_0 p_{n,f_0}(f_0) df_0 \leq P^x_{FA}$  6)

and $P_D^y = \int_0^1 f_1 p_{n,f_0}(f_0) df_0,$  (17)

where $p_{n,f_0}(\cdot)$ is the SR noise pdf in the $f_0$ domain.

Compared to the original conditions 1), 2) and 3), this equivalent form has some advantages. First, the problem complexity is dramatically reduced. Instead of searching for an optimal solution in $R^N$, the present invention seeks an optimal solution in a single dimensional space. Second, by applying these new conditions, the present invention avoids the direct use of the underlying pdfs $p_1(\cdot)$ and $p_o(\cdot)$ and replace them with $f_1$ and $f_0$. Note that, in some cases, it is not very easy to find the exact form of $f_0$ and $f_1$. However, recall that $F_1(x_0)$ and $F_0(x_0)$ are the Probability of Detection and Probability of False Alarm, respectively, of the original system with input $x+x_o$. In practical applications, the relationship may be determined by Monte Carlo simulation using importance sampling. In general, compared to $p_1$ and $p_o$, $f_1$ and $f_0$ are much easier to estimate and once the optimum $p_{n,f_0}$ is found, the optimum $p_n(x)$ is determined as well by the inverse of the functions $F_0$ and $F_1$.

Consider the function J(t), such that $J(t) = \sup(f_1 : f_0 = t)$ is the maximum value of $f_1$ given $f_0$. Clearly, $J(P^x_{FA}) \geq F_1(0) = P^x_D$. It follows that for any noise $p_n$, $P_D^y(p_n) = \int_0^1 J(f_0) p_{n,f_0}(f_0) df_0$  (18)

Therefore, the optimum $P_D^y$ is attained when $f_1(f_0) = J(f_0)$ and $P_{D,opt}^y = E_n(J)$.

Improvability of a given detector when SR noise is added can be determined by computing and comparing $p_{D,opt}^y$ and $P_D^x$. When $P_{D,opt}^y > P_D^x$, the given detector is improvable by adding SR noise. However, it requires the complete knowledge of $F_1(\cdot)$ and $F_0(\cdot)$ and significant computation. For a large class of detectors, however, depending on the specific properties of J, it is possible to determine the sufficient conditions for improvability and non-improvability more easily. The conditions are determined using the following theorems.

Theorem 1 (Improvability of Detection via SR): If $J(P^x_{FA}) > P_D^x$ or $J''(P^x_{FA}) > 0$ when J(t) is second order continuously differentiable around $P^x_{FA}$, then there exists at least one noise process n with pdf $p_n(\cdot)$ that can improve the detection performance.

Proof: First, when $J(P^x_{FA}) > P_D^x$, from the definition of J function, we know that there exists at one least one $n_0$ such that $F_0(n_0) = P^x_{FA}$ and $F_1(n_0) = J(P^x_{FA}) > P_D^x$. Therefore, the detection performance can be improved by choosing a SR noise pdf $P_n(n) = \delta(n-n_0)$. When $J''(P^x_{FA}) > 0$ and is continuous around $P^x_{FA}$, there exists an $\epsilon > 0$ such that $J''(\cdot) > 0$ on $I = (P^x_{FA} - \epsilon, P^x_{FA} + \epsilon)$. Therefore, from Theorem A-1, J is convex on I. Next, add noise n with pdf $p_n(x) = \frac{1}{2}\delta(x-x_0) + \frac{1}{2}\delta(x+x_0)$, where $F_0(x_0) = P^x_{FA} - \epsilon/2$ and $F_0(x_1) = P^x_{FA} - \epsilon/2$. Due to the convexity of J, $$P_D^y = \frac{J\left(P^x_{FA} - \frac{\epsilon}{2}\right) + J\left(P^x_{FA} - \frac{\epsilon}{2}\right)}{2} > J(P^x_{FA}) \geq P_D^x$$

Thus, detection performance can be improved via the addition of SR noise.

Theorem 2 (Non-improvability of Detection via SR): If there exists a non-decreasing concave function $\Psi(f_0)$ where $\Psi(P^x_{FA}) = J(P^x_{FA}) = F_1(0)$ and $\Psi(f_0) \geq J(f_0)$ for every $f_0$, then $P_D^y \leq P_D^x$ for any independent noise, i.e., the detection performance cannot be improved by adding noise.

Proof: For any noise n and corresponding y, we have $$P_D^y(p_n) = \int_0^1 J(f_0) p_{n,f_0}(f_0) df_0 \leq \int_0^1 \Psi(f_0) p_{n,f_0}(f_0) df_0 \leq \qquad (19)$$
$$\Psi\left(\int_0^1 f_0 p_{n,f_0}(f_0) df_0\right) \leq \Psi(P^x_{FA}) = P_D^x$$

The third inequality of the Right Hand Side (RHS) of (19) is obtained using the concavity of the Ψ function. The detection performance cannot be improved via the addition of SR noise.

Before determining the form of the optimum SR noise pdf, i.e., the exact pdf of $p_n^{opt}$, the following result for the form of optimum SR noise must be determined.

Theorem 3 (Form of Optimum SR Noise): To maximize $P_D^y$, under the constraint that $P_{FA}^y \le P_{FA}^x$, the optimum noise can be expressed as:

$$p_n^{opt}(n) = \lambda \delta(n-n_1) + (1-\lambda)\delta(n-n_2) \quad (20)$$

where $0 \le \lambda \le 1$. In other words, to obtain the maximum achievable detection performance given the false alarm constraints, the optimum noise is a randomization of two discrete vectors added with the probability $\lambda$ and $1-\lambda$, respectively.

Proof: Let $U = \{(f_1, f_0) | f_1 = F_1(x), f_0 = F_0(x), x \in R^N\}$ be the set of all pairs of $(f_1; f_0)$. Since $0 \le f_1; f_0 \le 1$, U is a subset of the linear space $R^2$. Furthermore, let V be the convex hull of U. Since $V \subset R^2$, its dimension Dim(V)≤2. Similarly, let the set of all possible $(P_D^y; P_{FA}^y)$ be W. Since any convex combination of the elements of U, say $$(\chi, \phi) = \sum_{i=1}^{M} \alpha_i (f_{1,i}, f_{0,i})$$

can be obtained by setting the SR noise pdf such that $$p_{n,f_0}(f_0) = \sum_{i=1}^{M} \alpha_i \delta(f_0 - f_{0,i})$$

$V \subseteq W$. It can also be shown that $W \subseteq V$. Otherwise, there would exist at least one element z such that $z \in W$, but $z \notin V$. In this case, there exists a small set S and a positive number τ such that $$S = \{(x, y) | \|(x, y) - z\|_2^2 < \tau\} \text{ and } S \cap V = \{ \}$$

where '{ }' denotes an empty set. However, since $0 \le f_1; f_0 \le 1$, by the well known property of integration, there always exists a finite set E with finite elements such that $E \subseteq U$ and $(x_1; y_1)$, a convex combination of the elements of E, such that $$\|(x_1, y_1) - z\|_2^2 < \tau$$

Since $(x_1; y_1) \in V$, then $(x_1; y_1) \in (V \cap S)$ which contradicts the definition of S. Therefore, $W \subseteq V$. Hence, W=V. From Theorem A-4, $(P_D^y; P_{FA}^y)$ can be expressed as a convex combination of three elements. Also, since we are only interested in maximizing $P_D$ under the constraint that $P_{FA}^y \le P_{FA}^x$, the optimum pair can only belong to B, the set of the boundary elements of V. To show this, let $(f_1^*; f_0^*)$ be an arbitrary non-boundary point inside V. Since there exists a $\tau > 0$ such that $(f_1^* + \tau, f_0^*) \in V$, then $(f_1^*; f_0^*)$ is inadmissible as an optimum pair. Thus, the optimum pair can only exist on the boundary and each z on the boundary of V can be expressed as the convex combination of only two elements in U. Hence, $$(P_{D,opt}^y, P_{FA,opt}^y) = \lambda(f_{11}, f_{01}) + (1-\lambda)(f_{12}, f_{02}) \quad (21)$$

where $(f_{11}; f_{01})$; $(f_{12}; f_{02}) \in U$, $0 \le \lambda \le 1$. Therefore, we have $$p_{n,f_0}^{opt} = \lambda \delta(f_0 - f_{01}) + (1-\lambda)\delta(f_0 - f_{02}) \quad (22)$$

Equivalently, $p_n^{opt}(n) = \lambda \delta(n-n_1) + (1-\lambda)\delta(n-n_2)$, where $n_1$ and $n_2$ are determined by the equations $$\begin{cases} F_0(n_1) = f_{01} \\ F_1(n_1) = f_{11} \\ F_0(n_2) = f_{02} \\ F_1(n_2) = f_{12} \end{cases} \quad (23)$$

Alternatively, the optimum SR noise can also be expressed in terms of $C_n$, such that $$C_n^{opt}(x) = \lambda \phi(x+n_1) + (1-\lambda)\phi(x+n_2) \quad (24)$$

From equation (22), we have $$P_{D,opt}^y = \lambda J(f_{01}) + (1-\lambda) J(f_{02}) \quad (25)$$

and $$P_{FA,opt}^y = \lambda f_{01} + (1-\lambda) f_{02} \le P_{FA}^x \quad (26)$$

Depending on the location of the maxima of $J(\cdot)$, determination of the pdf of optimum SR noise may be accomplished according to the following theorem.

Theorem 4: Let $F_{1M} = \max(J(t))$ and $$t_0 = \arg\min_t (J(t) = F_{1M}).$$

It follows that

Case 1: If $t_o \le P_{FA}^x$, then $P_{FA,opt}^x = t_o$ and $P_{D,opt}^y = F_{1M}$, i.e., the maximum achievable detection performance is obtained when the optimum noise is a DC signal with value no, i.e., $$p_n^{opt}(n) = \delta(n - n_0) \quad (27)$$

where $F_0(n_o) = t_o$ and $F_1(n_o) = F_{1M}$.

Case 2: If $t_o > P_{FA}^x$, then $P_{FA,opt}^x = F_0(0) = P_{FA}^x$, i.e., the inequality of (26) becomes equality. Furthermore, $$P_{FA,opt}^y = \lambda f_{01} + (1-\lambda) f_{02} = P_{FA}^x \quad (28)$$

Proof: For Case 1, notice that $$P_D^y = \int_0^1 J(f_0) p_{n,f_0}(f_0) df_0 \le \int_0^1 F_{1M} p_{n,f_0}(f_0) df_0 = F_{1M}$$

and $F_1(n_0) = F_{1M}$. Therefore the optimum detection performance is obtained when the noise is a DC signal with value $n_0$ with $P_{FA}^y = t_0$.

The contradiction method is used to prove Case 2. First, supposing that the optimum detection performance is obtained when $P_{FA,opt}^y = \kappa < P_{FA}^x$ with noise pdf $p_{n,f_0}^{opt}(f_0)$. Let $$p_{n_1,f_0}(f_0) = \frac{P_{FA}^x - \kappa}{t_0 - \kappa} \delta(f_0 - t_0) + \frac{t_0 - P_{FA}^x}{t_0 - \kappa} p_{n,f_0}^{opt}(f_0).$$

It is easy to verify that $p_{n,f_0}(f_0)$ is a valid pdf. Let $y_1 = x + n1$. We now have $$P_{FA}^{y_1} = \frac{P_{FA}^x - \kappa}{t_0 - \kappa} t_0 + \frac{t_0 - P_{FA}^x}{t_0 - \kappa} \kappa = P_{FA}^x,$$

and $$P_D^{y_1} = \frac{P_{FA}^x - \kappa}{t_0 - \kappa} F_{1M} + \frac{t_0 - P_{FA}^x}{t_0 - \kappa} P_{D,opt}^y > P_{D,opt}^x$$

But this contradicts (15), the definition of $p_n^{opt}$. Therefore, $P_{FA,opt}^y = P_{FA}^x$, i.e., the maximum achievable detection performance is obtained when the probability of false alarm remains the same for the SR noise modified observation y.

Figure 4:
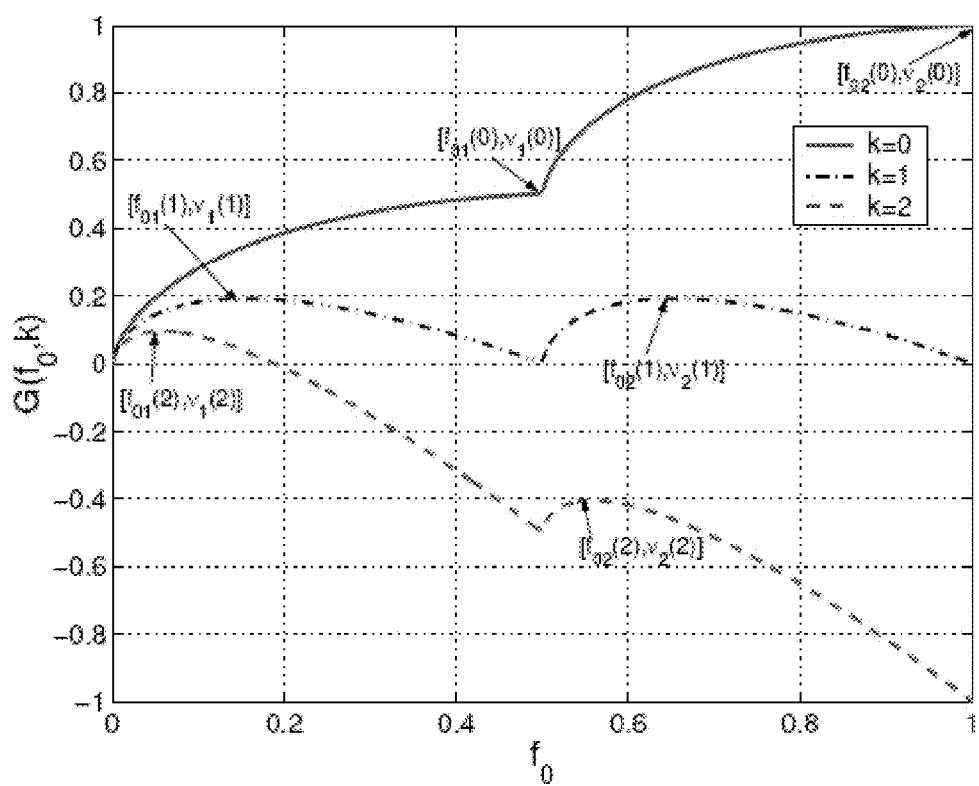
FIG. 4 is a graph of the relationship between $G(f_0; k)$, $f_0$, $f_{0i}(k)$, $v_i(k)$ with i=1, 2 and different k value 0, 1 and 2 according to the present invention.

For Case 2 of Theorem 4, i.e., when $t_0 > P_{FA}^x$, let us consider the following construction to derive the form of the optimum noise pdf. From Theorem 4, we have the condition that $P_{FA,opt}^y = F_0(0) = P_{FA}^x$ is a constant. Define an auxiliary function G such that $$G(f_0, k) = J(f_0) - kf_0, \quad (29)$$

where $k \in R$. We have $P_D^y = E_n(J) = E_n(G(f_0, k)) + kE_n(f_0) = E_n(G(f_0; k)) + kP_{FA}^x$. Hence, $p_{n,f_0}^{opt}$ also maximizes $E_n(G(f_0; k))$ and vice versa. Therefore, under the condition that $P_{FA}^y = P_{FA}^x$, maximization of $P_D^y$ is equivalent to maximization of $E_n(G(f_0; k))$. Divide the domain of $f_0$ into two intervals $I_1 = [0, P_{FA}^x]$ and $I_2 = [P_{FA}^x, 1]$. Let $f_{01}(k)$ be the minimum value that maximizes $G(f_0; k)$ in $I_1$ and let $f_{02}(k)$ be the minimum value that maximizes $G(f_0; k)$ in $I_2$. Also, let $v_1(k) = G(f_{01}; k)$ and $v_2(k) = G(f_{02}; k)$ be the corresponding maximum values. Since for any $f_0$, $G(f_0; k)$ is monotonically decreasing when $k$ is increasing, $v_1(k)$ and $v_2(k)$ are monotonically decreasing while $f_{01}(k)$ and $f_{02}(k)$ are monotonically non-increasing when $k$ is increasing. Since $G(f_0; 0) = J$, therefore $v_2(0) = F_{1M} > v_1(0)$, furthermore, when $k$ is very large, we have $v_1(k) = J(0) > v_2(k) = J(P_{FA}^x) - kP_{FA}^x$. Hence, there exists at least one $k_0 > 0$ such that $v_1(k_0) = v_2(k_0) \equiv v$. For illustration purposes, the plots of $G(f_0; k)$ for the detection problem discussed below are shown in FIG. 4. Divide the [0,1] interval into two non-overlapping parts A, $\{f_{01}(k_0), f_{02}(k_0)\}$, such that $\{f_{01}(k_0); f_{02}(k_0)\} \cup A = [0, 1]$ and $\{f_{01}(k_0); f_{02}(k_0)\} \cap A = \{\}$. Next, represent $p_{n,f_0}(f_0)$ as $$p_{n,f_0}(f_0) = \alpha_1 \delta(f_0 - f_{01}(k_0)) + \alpha_2 \delta(f_0 - f_{02}(k_0)) + I_A(f_0) p_{n,f_0}(f_0) \quad (30)$$

where $I_A(f_0) = 1$ for $f_0 \in A$ and is zero otherwise (an indicator function). From equation (5), we must have $$\alpha_1 + \alpha_2 + \int_A p_{n,f_0} df_0 = 1, \quad (31)$$

and $$E_n(G) = (\alpha_1 + \alpha_2)v + \int_A G(f_0, k_0) p_{n,f_0} df_0 \quad (32)$$

$$= v + \int_A \underbrace{(G(f_0, k_0) - v)}_{\leq 0} p_{n,f_0} df_0 \leq v$$

Note that $J(f_0) \leq v$ for all $f_0 \in A$. Clearly, the upper bound can be attained when $p_{n,f_0} = 0$ for all $f_0 \in A$, i.e., $\alpha_1 + \alpha_2 = 1$. Therefore, $P_{D,opt}^y P_{D,opt}^y = E_n(G) + k_0 P_{FA}^x = v + k_0 P_{FA}^x$. From equation (28), we have $$p_{n,f_0}^{opt}(f_0) = \quad (33)$$

$$\frac{f_{02}(k_0) - P_{FA}^x}{f_{02}(k_0) - f_{01}(k_0)} \delta(f_0 - f_{01}(k_0)) + \frac{P_{FA}^x - f_{01}(k_0)}{f_{02}(k_0) - f_{01}(k_0)} \delta(f_0 - f_{02}(k_0))$$

Notice that by letting $$\lambda = \frac{f_{02}(k_0) - P_{FA}^x}{f_{02}(k_0) - f_{01}(k_0)},$$

(33) is equivalent to (22).

Equivalently, we have the expression of $p_n^{opt}(n)$ as $$p_n^{opt}(n) = \frac{f_{02}(k_0) - P_{FA}^x}{f_{02}(k_0) - f_{01}(k_0)} \delta(n - n_1) + \frac{P_{FA}^x - f_{01}(k_0)}{f_{02}(k_0) - f_{01}(k_0)} \delta(n - n_2) \quad (34)$$

Further, in the special case where $f_1$ is continuously differentiable, G is also continuously differentiable. Since $f_{01}$ and $f_{02}$ are at least local maxima, we have $$\frac{\partial G}{\partial f_0}(f_{01}, k_0) = \frac{\partial G}{\partial f_0}(f_{02}, k_0) = 0$$

Therefore, from the derivative of (29), we have $$\frac{dJ}{df_0}(f_{01}(k_0)) = \frac{dJ}{df_0}(f_{02}(k_0)) = k_0 \quad (35) \text{ and } (36)$$

$$J(f_{02}(k_0)) - J(f_{01}(k_0)) = k_0(f_{02}(k_0) - (f_{01}(k_0))$$

In other words, the line connecting $(J(f_{01}(k_0)), f_{01}(k_0))$ and $(J(f_{02}(k_0)), f_{02}(k_0))$ is the bi-tangent line of $J(\cdot)$ and $k_0$ is its slope. Also, $$P_{D,opt}^y = v + k_0 P_{FA}^x \quad (37)$$

Thus, the condition under which SR noise can improve detection performance has been derived, and the specific form of the optimum SR noise has been obtained.

Detection Example

In a detection problem where two hypotheses H0 and H1 are given as $$\begin{cases} H_0: x[i] = w[i] \\ H_1: x[i] = A + w[i], \end{cases} \quad (38)$$

for $i = 0, 1, \ldots, N-1$, $A > 0$ is a known dc signal, and $w[i]$ are i.i.d noise samples with a symmetric Gaussian mixture noise pdf as follows $$p_w(w) = \frac{1}{2}\gamma(w; -\mu, \sigma_0^2) + \frac{1}{2}\gamma(w; \mu, \sigma_0^2) \quad (39)$$

where $$\gamma(w; \mu, \sigma_0^2) = \frac{1}{\sqrt{2\pi\sigma^2}} \exp\left[-\frac{(w-\mu)^2}{2\sigma^2}\right]$$

setting $\mu = 3$, $A = 1$ and $\sigma_0 = 1$. A suboptimal detector is considered with test statistic $$T(x) = \frac{1}{N}\sum_{i=0}^{N-1}\left(\frac{1}{2} + \frac{1}{2}\text{sgn}(x[i])\right) = \frac{1}{N}\sum_{i=0}^{N-1}(\bar{\omega}_x[i]) \quad (40)$$

where $$\bar{\omega}_x[i] = \frac{1}{2} + \frac{1}{2}\text{sgn}(x[i]).$$

From equation (40), this detector is essentially a fusion of the decision results of N i.i.d. sign detectors.

When N=1, the detection problem reduces to a problem with the test statistic $T_1(x)=x$, threshold $\eta=0$ (sign detector) and the probability of false alarm $P_{FA}{}^x=0.5$. The distribution of x under the $H_0$ and $H_1$ hypotheses can be expressed as $$p_0(x) = \frac{1}{2}\gamma(x; -\mu, \sigma_0^2) + \frac{1}{2}\gamma(x; \mu, \sigma_0^2) \tag{41}$$

and $$p_1(x) = \frac{1}{2}\gamma(x; -\mu+A, \sigma_0^2) + \frac{1}{2}\gamma(x; \mu+A, \sigma_0^2) \tag{42}$$

respectively. The critical function is given by $$\phi(x) = \begin{cases} 1 & x > 0 \\ 0 & x \leq 0. \end{cases} \tag{43}$$

The problem of determining the optimal SR noise is to find the optimal p(n) where for the new observation $y=x+n$, the probability of detection $P_D{}^y = p(y>0; H_1)$ is maximum while the probability of false alarm $P_{FA}{}^y = p(y>0; H_0) \leq P_{FA}{}^x = \frac{1}{2}$.

When N>1, the detector is equivalent to a fusion of N individual detectors and the detection performance monotonically increases with N. Like the N=1 case, when the decision function is fixed, the optimum SR noise can be obtained by a similar procedure. Due to space limitations, only the suboptimal case where the additive noise n is assumed to be an i.i.d noise is considered here. Under this constraint, since the $P_D$s and $P_{FA}$s of each detector are the same, it can be shown that the optimal noise for the case N>1 is the same as N=1 because $P_{FA} \leq 0.5$ is fixed for each individual detector while increasing its $P_D$. Hence, only the one sample case (N=1) is considered below. However, the performance of the N>1 case can be derived similarly.

The determination of the optimal SR noise pdf follows from equations (11) and (13), where it can be shown that in this case, $$F_1(x) = \int_0^{+\infty} \phi(y) p_1(y-x) dy \tag{44}$$

$$= \frac{1}{2}\left(\int_0^{+\infty} [\gamma(y-x; -\mu+A, \sigma_0^2) + \gamma(y-x; \mu+A, \sigma_0^2)] dy\right)$$

$$= \frac{1}{2}Q\left(\frac{-x-\mu-A}{\sigma_0}\right) + \frac{1}{2}Q\left(\frac{-x+\mu-A}{\sigma_0}\right)$$

and $$F_0(x) = \int_0^{+\infty} \phi(y) p_0(y-x) dy \tag{45}$$

$$= \frac{1}{2}\left(\int_0^{+\infty} [\gamma(y-x; -\mu, \sigma_0^2) + \gamma(y-x; \mu, \sigma_0^2)] dy\right)$$

$$= \frac{1}{2}Q\left(\frac{-x-\mu}{\sigma_0}\right) + \frac{1}{2}Q\left(\frac{-x+\mu}{\sigma_0}\right)$$

where $$Q(x) = \int_x^{\infty} \frac{1}{\sqrt{2\pi}} \exp(-t^2/2) dt.$$

Figure 2:
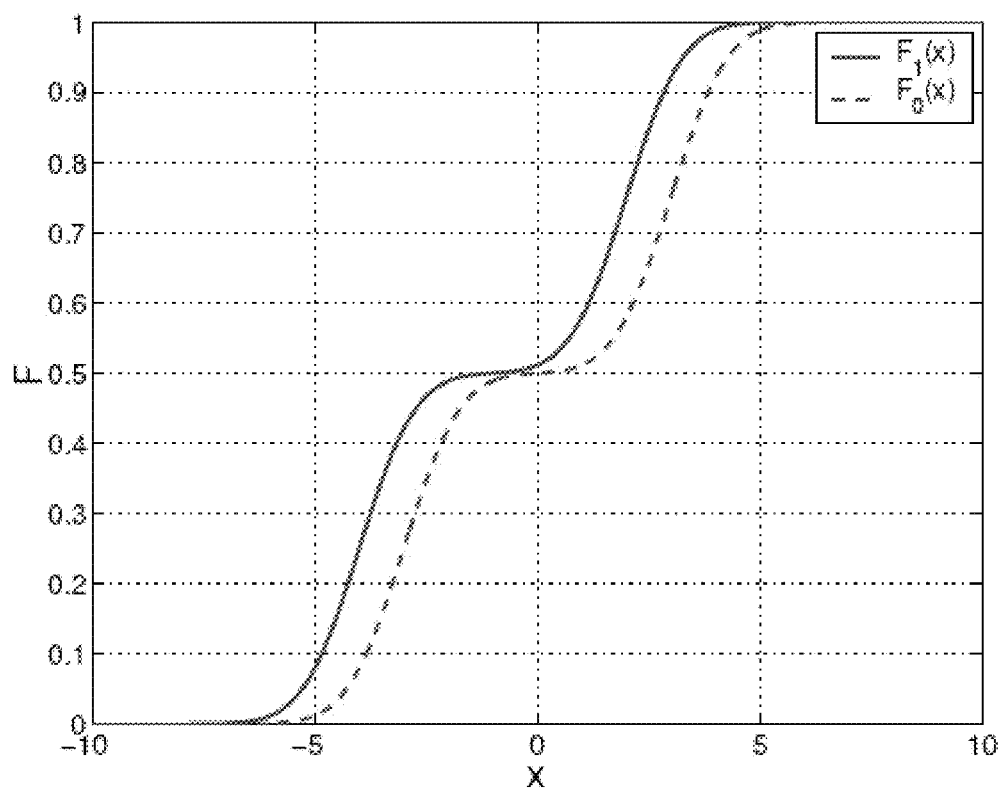
FIG. 2 is a graph of the values of $F_1$ and $F_0$ as a function of x according to the present invention.
Figure 3:
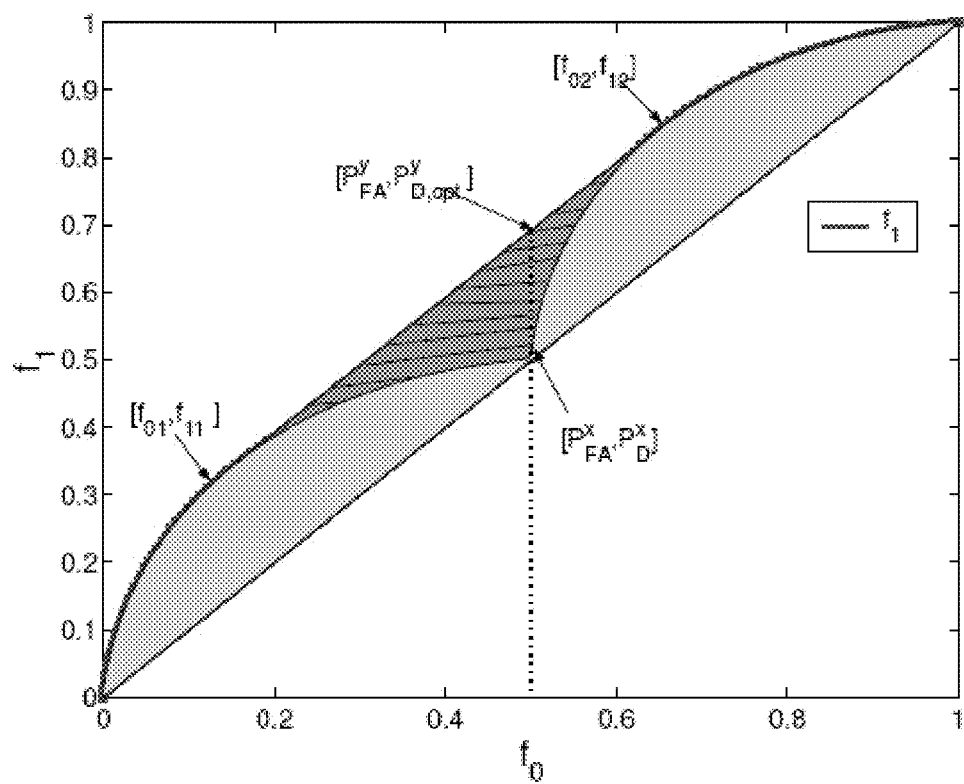
FIG. 3 is a graph of the relationship between $f_1$ and $f_0$ according to the present invention.

It is also easy to show that, in this case, $F_1(x) > F_0(x)$ and both are monotonically increasing with x. Therefore, $J(f_0)=f_1(f_0)=f_1$, and $U=(f_1; f0)$ is a single curve. FIG. 2 shows the values of $f_1$ and $f_0$ as a function of x, while the relationship between $F_1$ and $F_0$ is shown in FIG. 3. V, the convex hull of all possible $P_D$ and $P_{FA}$ after n is added and shown as the light and dark shadowed regions in FIG. 3. Note that a similar non-concave ROC occurs in distributed detection systems and dependent randomization is employed to improve system performance. Taking the derivative of $f_1$ w.r.t. $f_0$, we have $$\frac{d(f_1)}{d(f_0)} = \frac{\frac{d(f_1)}{dx}}{\frac{d(f_0)}{dx}} = \frac{p_1(-x)}{p_0(-x)}, \tag{46}$$

and $$\frac{d^2(f_1)}{d(f_0^2)} = \frac{1}{p_0(-x)} \frac{d\left(\frac{p_1(-x)}{p_0(-x)}\right)}{dx} \tag{47}$$

$$= \frac{-p_1'(-x)p_0(-x) + p_0'(-x)p_1(-x)}{p_0^3(-x)};$$

where $x = F_0^{-1}(f_0)$. Since $$\frac{d\gamma(y-x; \mu, \sigma^2)}{dx} = \frac{\mu-x}{\sigma^2}\gamma(y-x; \mu, \sigma^2)$$

we have $p'_0(-x)|_{x=0}$ and $$\left.\frac{d^2(f_1)}{d(f_0^2)}\right|_{f_0=f_0(0)} = \left.\frac{-p_1'(-x)p_0(-x) + p_0'(-x)p_1(-x)}{p_0^3(-x)}\right|_{x=0} \tag{48}$$

$$= \left.\frac{-p_1'(-x)}{p_0^2(-x)}\right|_{x=0}$$

$$= \frac{(\mu-A)\exp\left(-\frac{(\mu-A)^2}{2\sigma_0^2}\right)}{\sqrt{2\pi}\,\sigma_0^3 p_0^2(0)} -$$

$$\frac{(\mu+A)\exp\left(-\frac{(\mu+A)^2}{2\sigma_0^2}\right)}{\sqrt{2\pi}\,\sigma_0^3 p_0^2(0)}.$$

With respect to the improvability of this detector, when $A<\mu$, setting (48) equal to zero and solving the equation for $\sigma_0$, we have $\sigma_1$, the zero pole of (48)

$$\sigma_1 = \sqrt{2\frac{\mu A}{\ln\left(\frac{\mu+A}{\mu-A}\right)}}.$$

When $\sigma_0 < \sigma_1$, then $$\left.\frac{d^2(f_1)}{d(f_0^2)}\right|_{f_0=F_0(0)} > 0$$

and, in this example, $\sigma_1^2=8.6562>\sigma_0^2=1$. From Theorem 1, this detector is improvable by adding independent SR noise. When $$A > \mu, \left.\frac{d^2(f_1)}{d(f_0^2)}\right|_{f_0=f_0(0)} < 0$$

the improvability cannot be determined by Theorem 1. However, for this particular detector, as discussed below, the detection performance can still be improved.

The two discrete values as well as the probability of their occurrence may be determined by solving equations (35) and (36). From equations (44) and (45), the relationship between $f_1$, $f_0$ and $x$, and equation (46), we have $$\frac{p_1(-n_1)}{p_0(-n_1)} = \frac{p_1(-n_2)}{p_0(-n_2)} \tag{49}$$

$$\frac{F_1(n_1) - F_1(n_2)}{F_0(n_1) - F_0(n_2)} = \frac{p_1(-n_2)}{p_0(-n_2)}.$$

Although it is generally very difficult to solve the above equation analytically, in this particular detection problem, $$p_1\left(-\left(\mu - \frac{A}{2}\right)\right) = 0.5\gamma\left(-\frac{A}{2}; 0, \sigma_0^2\right) + 0.5\gamma\left(2\mu + \frac{A}{2}; 0, \sigma_0^2\right),$$

$$p_0\left(-\left(\mu - \frac{A}{2}\right)\right) = 0.5\gamma\left(-\frac{A}{2}; 0, \sigma_0^2\right) + 0.5\gamma\left(2\mu - \frac{A}{2}; 0, \sigma_0^2\right),$$

$$p_1\left(-\left(-\mu - \frac{A}{2}\right)\right) = 0.5\gamma\left(-\frac{A}{2}; 0, \sigma_0^2\right) + 0.5\gamma\left(2\mu - \frac{A}{2}; 0, \sigma_0^2\right),$$

$$p_0\left(-\left(-\mu - \frac{A}{2}\right)\right) = 0.5\gamma\left(-\frac{A}{2}; 0, \sigma_0^2\right) + 0.5\gamma\left(2\mu + \frac{A}{2}; 0, \sigma_0^2\right),$$

so that $$\frac{p_1\left(-\left(\mu - \frac{A}{2}\right)\right)}{p_0\left(-\left(\mu - \frac{A}{2}\right)\right)} \cong 1, \quad \frac{p_1\left(-\left(-\mu - \frac{A}{2}\right)\right)}{p_0\left(-\left(-\mu - \frac{A}{2}\right)\right)} \cong 1$$

and $$F_1\left(\left(\mu - \frac{A}{2}\right)\right) - F_1\left(\left(-\mu - \frac{A}{2}\right)\right) = F_0\left(\left(\mu - \frac{A}{2}\right)\right) - F_0\left(\left(-\mu - \frac{A}{2}\right)\right)$$

given $2\mu - A/2 > 3\sigma_0$. Thus, the roots $n_1$; $n_2$ of equation (49) can be approximately expressed as $n_1 = -\mu - A/2$ and $n_2 = \mu - A/2$. Correspondingly, $$\lambda = \frac{F_0(n_2) - F_0(0)}{F_0(n_2) - F_0(n_1)} \text{ and } 1 - \lambda = \frac{F_0(0) - F_0(n_1)}{F_0(n_2) - F_0(n_1)}. \tag{50}$$

Hence $$p_n^{opt}(n) = \lambda\delta(n - n_1) + (1 - \lambda)\delta(n - n_2)$$
$$= 0.3085\delta(n + 3.5) + 0.6915\delta(n - 2.5),$$

and $$P_{D,opt}^y = \lambda F_1(n_1) + (1 - \lambda)F_1(n_2) = 0.6915. \tag{51}$$

The present invention also encompasses special cases where the SR noise is constrained to be symmetric. These include symmetric noise with arbitrary pdf $p_s(x)$, white Gaussian noise $p_g(x) = \gamma(x; 0, \sigma^2)$ and white uniform noise $p_u(x) = 1/a$, $a > 0$, $-a/2 \leq x \leq a/2$. The noise modified data processes are denoted as $y_s$, $y_g$ and $y_u$, respectively. Here, for illustration purposes, the pdfs of these suboptimal SR noises may be found by using the $C(x)$ functions. The same results can be obtained by applying the same approach as in the previous subsection using $F_1(\cdot)$ and $F_0(\cdot)$ functions. For the arbitrary symmetrical noise case, we have the condition $$p_s(x) = p_s(-x). \tag{52}$$

Therefore, $p(y|H_0)$ is also a symmetric function, so that $P_{FA}^{y_s} = \frac{1}{2}$. By equations (43) and (52), we have $$C_s(x) = \int_0^\infty p_s(t - x) dt \tag{53}$$

$$= \int_{-x}^\infty p_s(t) dt$$

$$= \int_{-\infty}^x p_s(t) dt$$

$$= 1 - C_s(-x).$$

Since $p_s(x) \geq 0$, we also have $C_s(x_1) \geq C_s(x_0)$ for any $x_1 \geq x_0$, $C_s(0) = 1/2$, $C_s(-\infty) = 0$, and $C_s(\infty) = 1$ (54) and (55)

Figure 5:
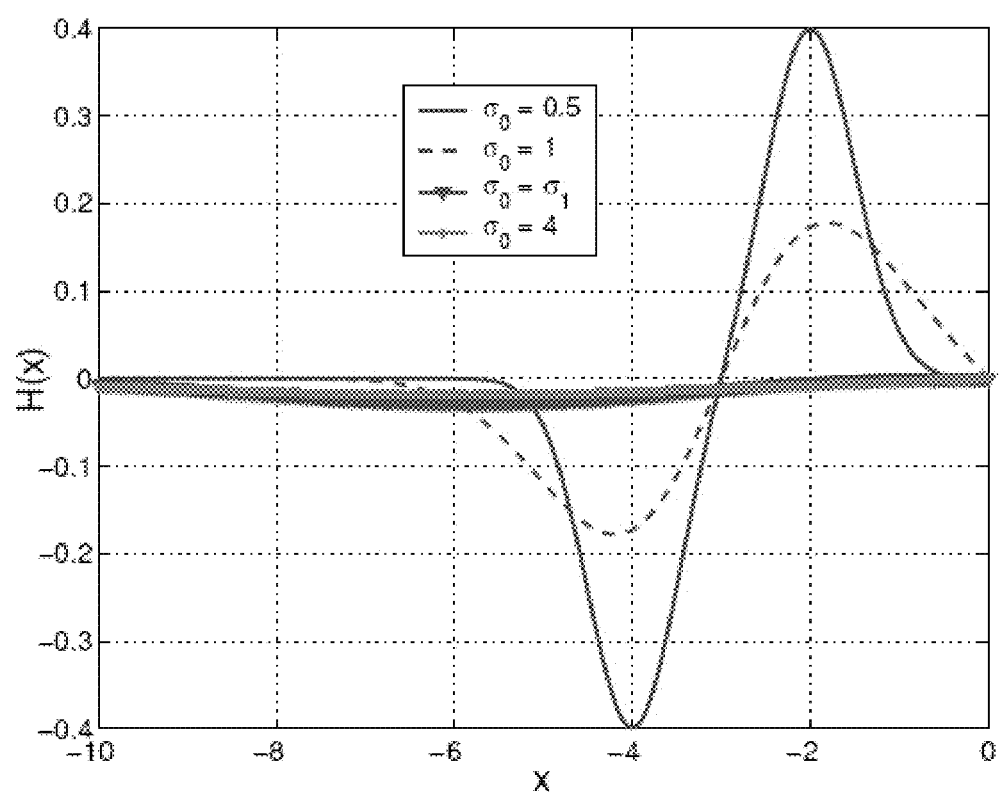
FIG. 5 is a graph illustrating different H(x) curves where μ=3, A=1 according to the present invention.

From equations (9) and (53), we have the $P_D$ of $y_s$ given by $$C_D^{y_s} = \int_{-\infty}^\infty p_1(x) C_s(x) dx \tag{56}$$

$$= \int_{-\infty}^0 p_1(x) C_s(x) dx + \int_0^\infty (1 - C_s(-x)) p_1(x) dx$$

$$= \int_{-\infty}^0 (p_1(x) - p_1(-x)) C_s(x) dx + P_D^x$$

$$= \int_{-\infty}^0 H(x) C_s(x) dx + P_D^x,$$

where $H(x) \equiv p_1(x) - p_1(-x)$. FIG. 5 shows a plot of $H(x)$ for several $\sigma_0$ values. Finally, from equation (42), we have $$p_1(-x) = \frac{1}{2}\gamma(x; \mu - A, \sigma_0^2) + \frac{1}{2}\gamma(x; -\mu - A, \sigma_0^2).$$

When $A \geq \mu$, since $p_1(-x) \geq p_1(x)$ when $x < 0$, we have, $H(x) < 0$, $x < 0$. From equation (56), $P_D^{y_s} \leq P_D^x$ for any $H(x)$, i.e., in this case, the detection performance of this detector cannot be improved by adding symmetric noise. When $A < \mu$ and $\sigma_0 \geq \sigma_1$ then $H(x) < 0$, $\forall x < 0$. Therefore, adding symmetric noise will not improve the detection performance as well. However, when $\sigma_0 < \sigma_1$, $H(x)$ has only a single root $x_0$ for $x < 0$ and $H(x) < 0$, $\forall x < x_0$, $H(x) > 0$, $\forall x \in (x_0, 0)$ and detection performance can be improved by adding symmetric SR noise. From equation (56), we have $$C_s^{opt}(x) = \begin{cases} 0, & x < x_0 \\ \frac{1}{2}, & x_0 \leq x \leq 0, \end{cases} \tag{57}$$

and

-continued
$$p_s^{opt} = \frac{1}{2}\delta(x - x_0) + \frac{1}{2}\delta(x + x_0).$$

Furthermore, since $\gamma(-\mu; -\mu-A,\sigma^2_0)=\gamma(-\mu; -\mu+A,\sigma^2_0)$ and $\gamma(-\mu; -\mu+A,\sigma^2_0)\approx 0$ given $2\mu-A>>\sigma_0$, we have $x_0\approx-\mu$. Therefore, $$p_s^{opt} = \frac{1}{2}\delta(x - \mu) + \frac{1}{2}\delta(x + \mu). \quad (58)$$

The pdf of y for the $H_1$ hypothesis becomes $$p_{1,y_s}^{opt}(y) = \frac{1}{2}\gamma(y; A, \sigma_0^2) + \frac{1}{4}\gamma(y; 2\mu + A, \sigma_0^2) + \frac{1}{4}\gamma(y; -2\mu + A, \sigma_0^2). \quad (59)$$

Hence, when $\mu$ is large enough, $$P_{D,opt}^{y_s} = \frac{1}{2}Q\left(-\frac{A}{\sigma_0}\right) + \frac{1}{4} = 0.6707.$$

Note that, as $\sigma_0$ decreases $P_{D,opt}^{y_s}$ increases, i.e., better detection performance can be achieved by adding the optimal symmetric noise.

Similarly, for the uniform noise case, $$C_u(x) = \int_{-x}^{\infty} p_u(t)dt = \begin{cases} 0, & x < \frac{-a}{2} \\ \frac{x}{a} + \frac{1}{2}, & -\frac{a}{2} \le x \le 0. \end{cases} \quad (60)$$

Substituting equation (60) for $C_s(x)$ in (56) and taking the derivative w.r.t a, we have $$\frac{dP_D^{y_s}}{da} = -\frac{1}{a^2}\int_{-\frac{a}{2}}^{0} xH(x)dx. \quad (61)$$

Setting it equal to zero and solving, we have $a_{opt}=8.4143$ in the pdf of uniform noise defined earlier. Additionally, we have $P_{D,opt}^{y_u}=0.6011$.

For the Gaussian case, the optimal WGN level is readily determined since $$P_D^{y_g} = \frac{1}{2}Q\left(\frac{-A-\mu}{\sqrt{\sigma_0^2 + \sigma^2}}\right) + \frac{1}{2}Q\left(\frac{-A-\mu}{\sqrt{\sigma_0^2 + \sigma^2}}\right). \quad (62)$$

Let $\sigma^2_2=\sigma^2_0+\sigma^2$ and take the derivative w.r.t $\sigma_2^2$ in equation (62), setting it equal to zero and solving, forming $$\sigma_2^2 = 2\frac{\mu A}{\ln\left(\frac{\mu + A}{\mu - A}\right)} = 8.6562, \quad (63)$$

and $\sigma^2_{opt}=\sigma^2_2-\sigma^2_0=7.6562$, and correspondingly, $P_{D,opt}^{y_g}=0.5807$. Therefore, when $\sigma^2_0<\sigma^2_2$, adding WGN with variance $\sigma^2_{opt}$ can improve the detection performance to a constant level $P^{y_g}_{D,opt}$.

Table 1 below is a comparison of detection performance for different SR noise enhanced detectors, and shows the values of $P_{D,opt}^{y}$ for the different types of SR noise. Compared to the original data process with $P_D^x=0.5114$, the improvement of different detectors are 0.1811, 0.1593, 0.0897 and 0.0693 for optimum SR noise, optimum symmetric noise, optimum uniform noise and optimum Gaussian noise enhanced detectors, respectively.

| SR Noise | $P_n^{opt}$ | $P_s^{opt}$ | $P_u^{opt}$ | $P_g^{opt}$ | No SR Noise |
|---|---|---|---|---|---|
| $P_D^y$ | .6915 | .6707 | .6011 | .5807 | .5115 |

Figure 6:
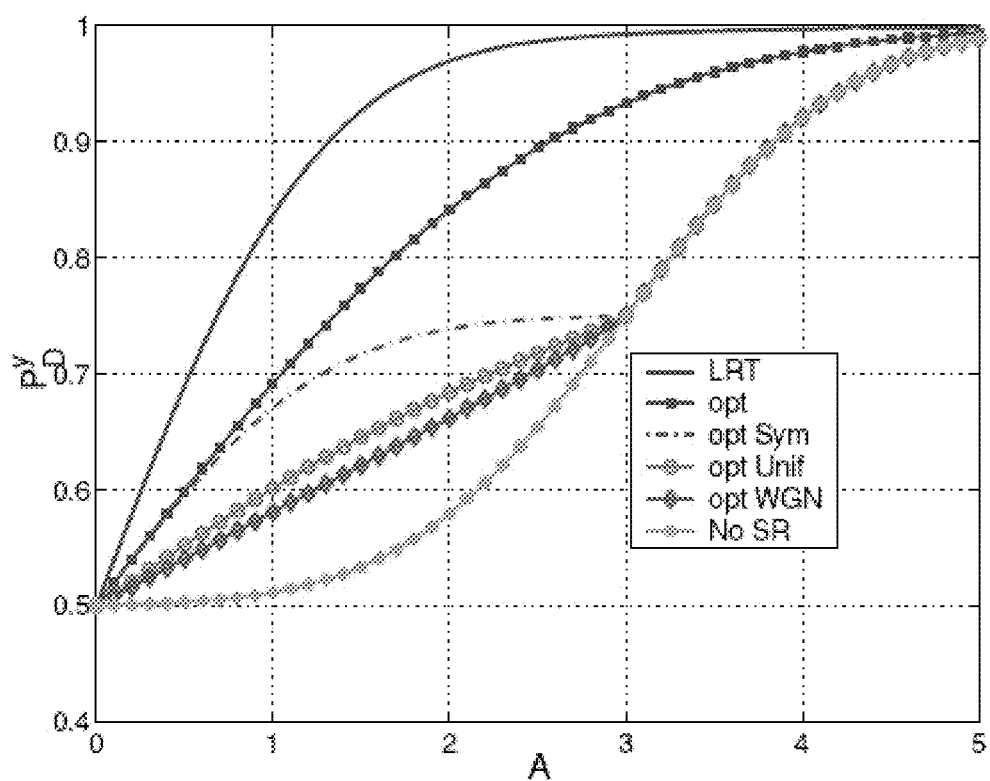
FIG. 6 is a graph of $P_D^y$ as a function of signal level A in Gaussian mixture noise when μ=3 and $\sigma_0$=1 according to the present invention.

FIG. 6 shows $P_D^x$ as well as the maximum achievable $P_D^y$ with different values of A. The detection performance is significantly improved by adding optimal SR noise. When $A\le\mu$, a certain degree of improvement is also observed by adding suboptimal SR noise. When A is small, $x_0\approx-\mu$ and $x_1\approx\mu$, the detection performance of the optimum SR noise enhanced detector is close to the optimum symmetric noise enhanced one. However, when A>0.6, the difference is significant. When A>$\mu$=3, H(x)<0; $\forall x<0$, so that $P_{D,opt}^{y_s}=P_{D,opt}^{y_u}=P_{D,opt}^{y_g}=P_D^x$, i.e, the optimal symmetric noise is zero (no SR noise). However, by adding optimal SR noise, $P_{D,opt}^{y}$ is still larger than $P_D^x$, i.e., the detection performance can still be improved. When $A\ge 5$, the $P_D$ improvement is not that significant because $P_D^x>0.97\approx 1$ which is already a very good detector.

Figure 7:
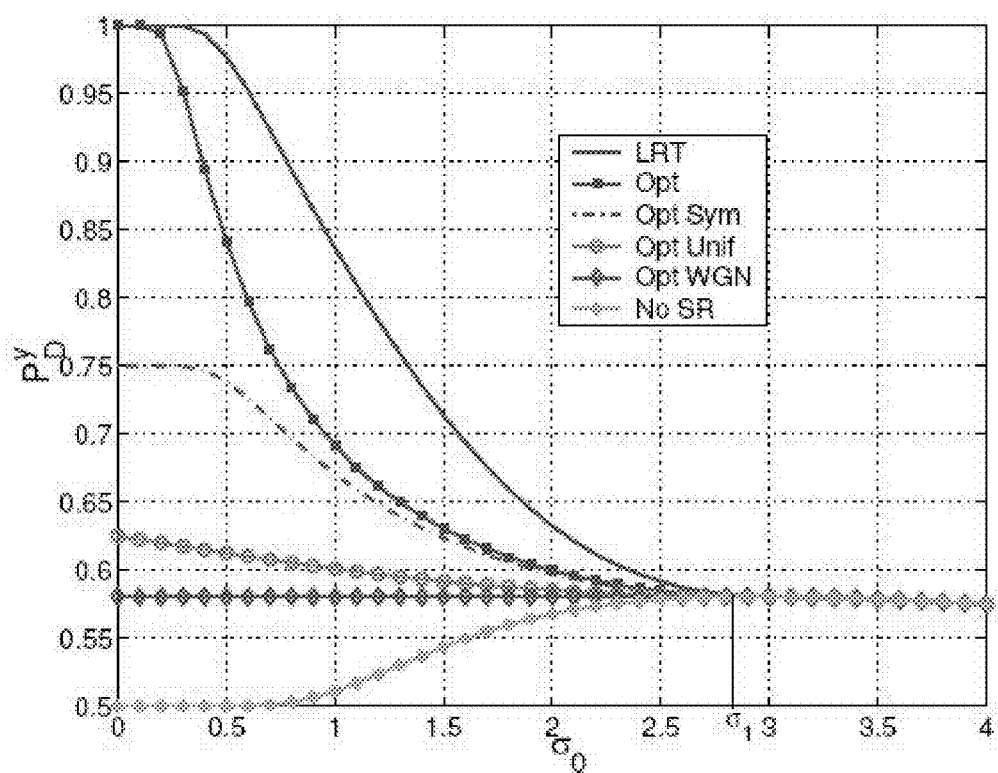
FIG. 7 is a graph of $P_D^y$ as a function of $\sigma_0$ for different types of noise enhanced detectors when μ=3 and A=1 according to the present invention.

The maximum achievable detection performance of different SR noise enhanced detectors with different background noise $\sigma_0$ is shown in FIG. 7. When $\sigma_0$ is small, for the optimum SR noise enhanced detectors $P_{D,opt}^{y}\approx 1$, while for the symmetric SR noise case $P_{D,opt}^{y_s}\approx 0.75$. When $\sigma_0$ increases, $P_D^x$ increases and the detection performance of SR noise enhanced detectors degrades. When $\sigma_0\ge\sigma_1$, $p_0(x)$ becomes a unimodal noise and the decision function $\phi$ is the same as the decision function decided by the optimum LRT test given the false alarm $P_{FA}=0.5$. Therefore, adding any SR noise will not improve $P_D$. Hence, all the detection results converge to $P_D^x$.

Figure 8:
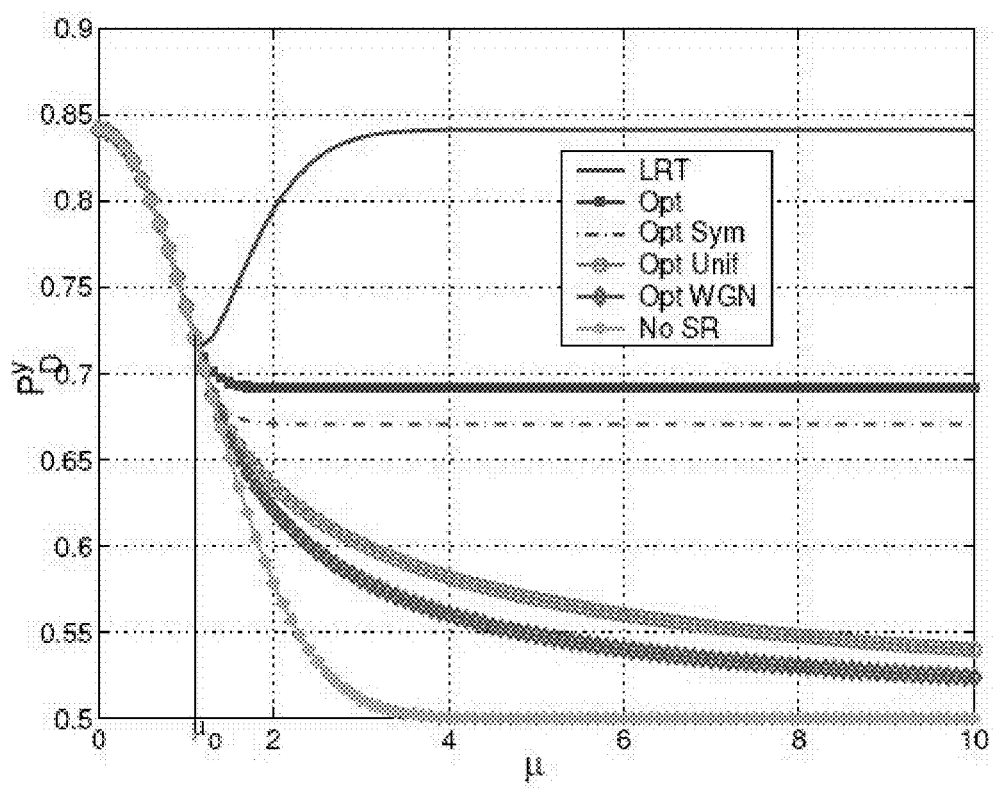
FIG. 8 is a graph of $P_D^y$ as a function of μ for different types of noise enhanced detectors when $\sigma_0$=1 and A=1 according to the present invention.

FIG. 8 compares the detection performance of different detectors w.r.t. $\mu$ when A=1 and $\sigma_0=1$ is fixed. $P_D^x$, $P_{D,opt}^{y_u}$ and $P_{D,opt}^{y_g}$ monotonically decreases when $\mu$ increases. Also, there exists a unique $\mu$ value $\mu_0$, such that when $\mu<\mu_0$ is small, $p_0$ is still a unimodal pdf, so that the decision function $\phi$ is the optimum one for $P_{FA}=0.5$. An interesting observation from FIG. 8 is that the $P_D$ of the "optimum LRT" after the lowest value is reached, increases when $\mu$ increases. The explanation of this phenomenon is that when $\mu$ is sufficiently large, the separation of the two peaks of the Gaussian mixtures increases as $\mu$ increases so that the detectability is increased. When $\mu\to\infty$, the two peaks are sufficiently separated, so that the detection performance of "LRT" is equal to the $P_D$ when $\mu=0$.

Figure 9:
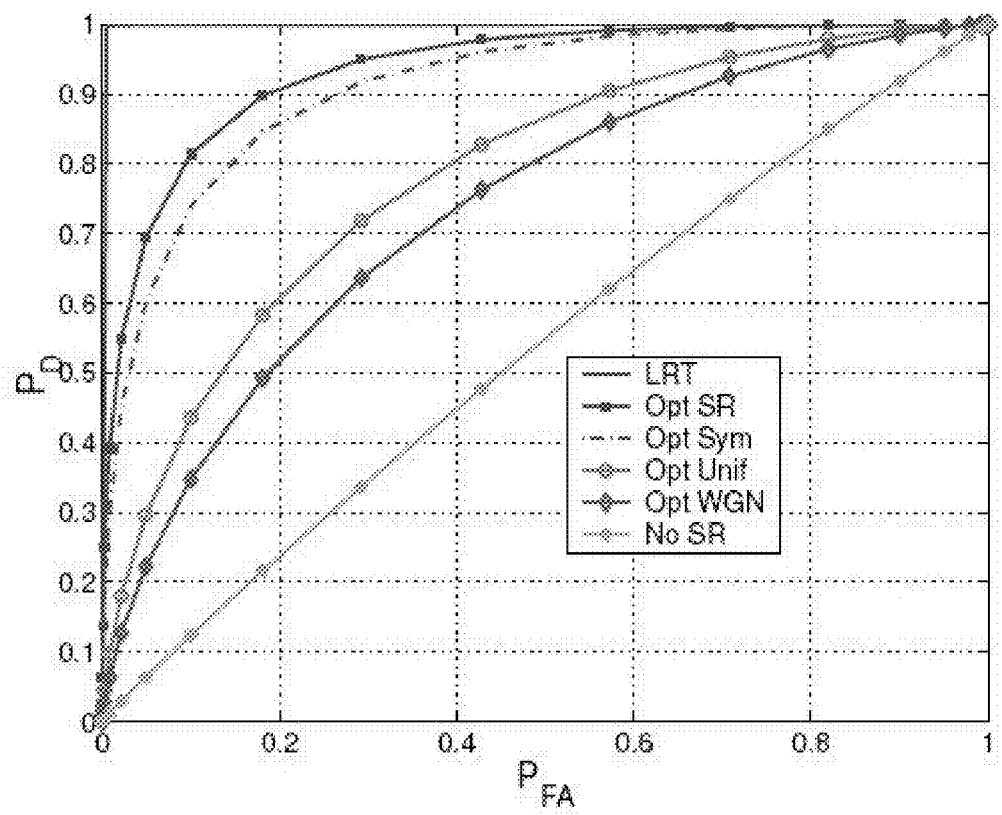
FIG. 9 is a graph of the ROC curves for different SR noise enhanced sign detectors when N=30 according to the present invention.

Finally, FIG. 9 shows the ROC curves for the detection problem when N=30 and the different types of i.i.d SR noise determined previously are added. Different degrees of improvement are observed for different SR noise pdfs. The optimum SR detector and the optimum symmetric SR detector performance levels are superior to those of the uniform and Gaussian SR detectors and more closely approximate the LRT curve. For LRT, the performance is nearly perfect ($P_D\approx 1$ for all $P_{FA}$s).

The present invention thus establishes a mathematical theory for the stochastic resonance (SR) noise modified detection problem, as well as several fundamental theorems on SR in detection theory. The detection performance of a SR noise enhanced detector is analyzed where, for any additive noise, the detection performance in terms of $P_D$ and $P_{FA}$ can be obtained by applying the expressions of the present invention. Based on these, the present invention established the conditions of potential improvement of $P_D$ via the SR effect, which leads to the sufficient condition for the improvability/non-improvability of most suboptimal detectors.

The present invention also established the exact form of the optimal SR noise pdf. The optimal SR noise is shown to be a proper randomization of no more than two discrete signals. Also, the upper limit of the SR enhanced detection performance is obtained by the present invention. Given the distributions $p_1$ and $p_0$, the present invention provides an approach to determine the optimal SR consisting of the two discrete signals and their corresponding weights. It should be pointed out that the present invention is applicable to a variety of SR detectors, e.g., bistable systems.

Figure 10:
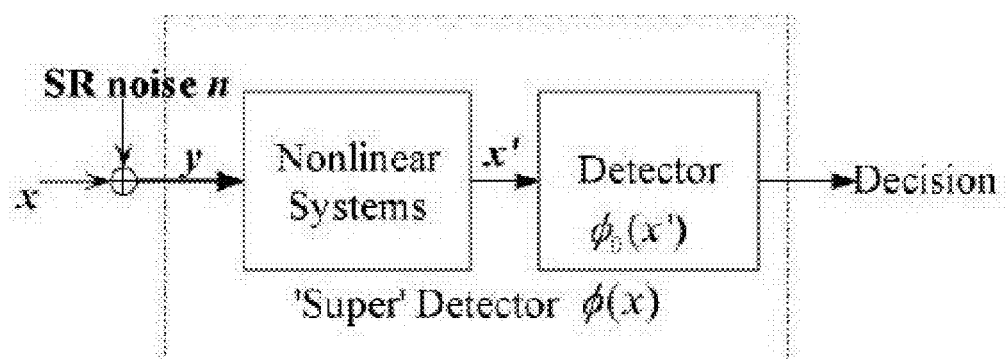
FIG. 10 is a schematic of an SR detection system according to the present invention.

The SR detectors that may be implemented with the present invention are shown in FIG. 10. For example, the nonlinear system block of FIG. 10 can depict the bistable system. Let $x=[x_1, x_2, \ldots, x_n]^T$ be the input to the nonlinear system, and $x'=[x_{01}, x_{02}, \ldots, x_N]^T$ be the output of the system as shown, where $x'=f(x)$ is the appropriate nonlinear function. The decision problem based on $x'$ can be described by decision function $\phi_0(\cdot)$ as shown. It is easy to observe that the corresponding decision function $\phi(\cdot)$ for the 'super' detector (i.e., the nonlinear system plus detector) is $\phi(x)=\phi_0(f(x))$. Thus, the SR detectors can be viewed as the system in FIG. 10 without the additive SR noise n. To summarize, the present invention admits conventional SR systems and allows improved detection system by adding n as shown in FIG. 10.

Figure 11:
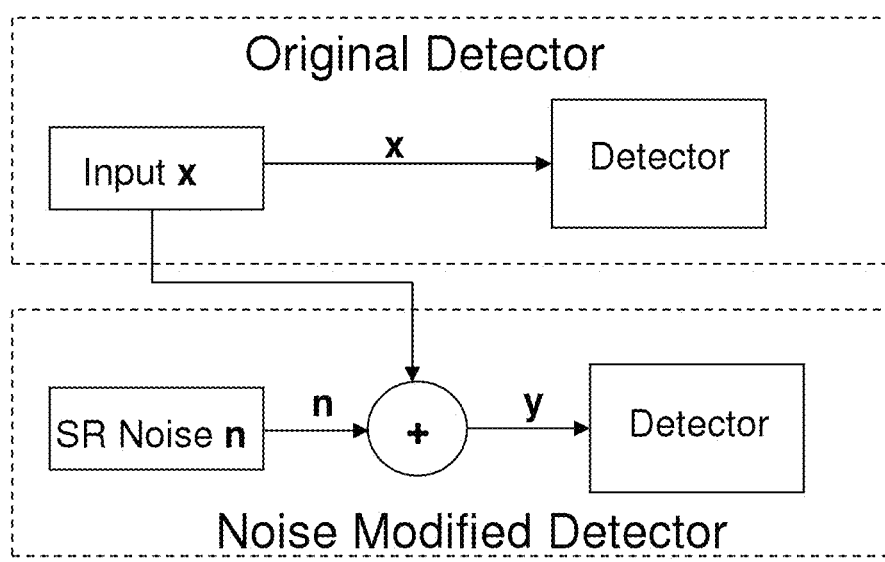
FIG. 11 is a schematic of an SR detection system according to the present invention.

FIG. 11 illustrates a diagram of a SR detection system obtained by a modification of the observed data, x. The statistical properties of the data are changed by adding independent SR noise n to yield a new process y such that $y=x+n$. This process, in turn is provided as input to the noise modified detector.

Based on the mathematical framework of the present invention, for a particular detection problem, the detection performance of six different detectors are compared, namely, the optimum LRT detector, optimum noise enhanced sign detector, optimum symmetric noise enhanced sign detector, optimum uniform noise enhanced sign detector, optimum Gaussian noise enhanced sign detector and the original sign detector. Compared to the traditional SR approach where the noise type is predetermined, much better detection performance is obtained by adding the proposed optimum SR noise to the observed data process. The present invention thus corresponds with the observed SR phenomenon in signal detection problems, and greatly advances the determination the applicability of SR in signal detection. The present invention can also be applied to many other signal processing problems such as distributed detection and fusion as well as pattern recognition applications.

The present invention may thus be used to increase the probability of detecting signals embedded in non-Gaussian noise. The first step is to record data from an observed data process. Next, stochastic resonance noise is added to said recorded. The appropriate stochastic resonance noise is controlled by determining the stochastic resonance noise probability density function (pdf) that does not increase the detector probability of false alarm.

The SR noise may be determined for the case of a known data probability density function by determining from the known probability density function of the observed data process the stochastic resonance noise pdf that equals $\lambda\delta(n-n_1)+(1-\lambda)\delta(n-n_2)$, with values $n_1$ and $n_2$ equal to those of the two delta function locations, and with probabilities equal to $\lambda$ and $(1-\lambda)$, respectively. More specifically, the stochastic resonance noise pdf may be calculated by determining $F_i(x)=\int_{R^N}\phi(y)p_i(y-x)dy$ $i=0,1$, using known critical function $\phi(y)$ and known data probability density functions $p_i(\cdot)$, $i=0,1$; determining the three unknown quantities $n_1$, $n_2$, and $\lambda$ using the known values $k_0$, $f_{01}$ and $f_{02}$ and the following three equations:

$$\frac{dJ}{df_0}(f_{01}(k_0)) = \frac{dJ}{df_0}(f_{02}(k_0)); \qquad \text{(i)}$$

$$\frac{dJ}{df_0}(f_{02}(k_0)) = k_0; \qquad \text{(ii)}$$

(iii) $J(f_{02}(k_0))-J(f_{01}(k_0))=k_0(f_{02}(k_0)-f_{01}(k_0))$; and determining the probability of occurrence for $n_1$ and $n_2$ as $\lambda$ and $1-\lambda$, respectively, using the equation $$\lambda = \frac{f_{02}(k_0) - P_{FA}^x}{f_{02}(k_0) - f_{01}(k_0)}.$$

Alternatively, the SR noise for the case of a known data probability density function may be calculated by determining the stochastic resonance noise pdf that consists of a single delta function, $\delta(n-n_0)$ with value $n_0$ equal to the delta function location with probability one. The minimum probability of error may be calculated from $$P_{e,min} = \pi_1\left[1 - \max_{f_0} G\left(f_0, \frac{\pi_0}{\pi_1}\right)\right]$$

where $G(f_0, k)=J(f_0)-kf_0=P_D-kP_{FA}$. The single delta function located at $n_0$ is calculated from $n_0=F_0^{-1}(f_0)$, where $f_0$ is the value the maximizes $$G\left(f_0, \frac{\pi_0}{\pi_1}\right).$$

The SR noise for the case of labeled data with an unknown data pdf may be determined by first calculating the stochastic resonance noise pdf that consists of two delta functions. This step is accomplished by estimating the stochastic resonance noise consisting of two random variables $n_1$ and $n_2$ by using many algorithms, such as expectation-maximization (EM) and the Karzen method to estimate the unknown data pdfs, and applying the estimated PDFs and the stochastic resonance noise pdf may be calculated by determining $F_i(x)=\int_{R^N}\phi(y)p_i(y-x)dY$ $i=0,1$, using known critical function $\phi(y)$ and known data probability density functions $p_i(\cdot)$, $i=0,1$; determining the three unknown quantities $n_1$, $n_2$, and $\lambda$ using the known value $k_0$, and estimated values $\hat{f}_{01}$, $\hat{f}_{02}$, and $\hat{J}$ in the following three equations:

$$\frac{d\hat{J}}{df_0}(\hat{f}_{01}(k_0)) = \frac{d\hat{J}}{df_0}(\hat{f}_{02}(k_0); \quad \text{(i)}$$

$$\frac{d\hat{J}}{df_0}(\hat{f}_{02}(k_0)) = k_0; \quad \text{(ii)}$$

(iii) $\hat{J}(\hat{f}_{02}(k_0)) - \hat{J}(\hat{f}_{01}(k_0)) = k_0(\hat{f}_{02}(k_0) - \hat{f}_{01}(k_0))$; and determining the probability of occurrence for $n_1$ and $n_2$ as $\lambda$ and $1-\lambda$, respectively, using the equation $$\lambda = \frac{\hat{f}_{02}(k_0) - P_{FA}^x}{\hat{f}_{02}(k_0) - \hat{f}_{01}(k_0)}.$$

The next step is to determine the stochastic resonance noise consisting of two random variables $n_1$ and $n_2$ with values equal to those of the two delta function locations and with probabilities equal to those of said stochastic resonance noise probability density function; adding said stochastic resonance noise to said data; applying said fixed detector to the resulting data process.

Finally, a test statistic for signal detection is calculated under a constant probability of false alarm rate (CFAR) constraint, such that the performance of suboptimal, nonlinear, fixed detectors operating in said non-Gaussian noise are improved. Increasing the probability of detecting signals embedded in non-Gaussian noise comprises adding the stochastic resonance noise $n_1$ and $n_2$ with probability $\lambda$ and $1-\lambda$, respectively, to the data, and applying the fixed detector to the resulting data process.

The present invention also provides a method for evaluating functions using $f_1$, $J(f_0)$, and $$\frac{dJ}{df_0}$$

where for any $f_0$, the equation $x = F_0^{-1}(f_0)$ is solved, and the value of $f_1$ is obtained by $$f_1 = F_1(x), \quad J(f_0) = \max_{f_1}(f_1(f_0)), \text{ and}$$

$$\frac{dJ}{df_0} = \lim_{\Delta \to 0} \frac{J(f_0 + \Delta) - J(f_0)}{\Delta}.$$

Following is background information relative to the formulas of the present invention and the applicable theorems on convex functions and convex sets.

A. Convex Functions

A function f: I→R is called convex if $$f(\lambda x + (1-\lambda)y) \leq \lambda f(x) + (1-\lambda)f(y) \quad (64)$$

for all x,y∈I and α in the open interval (0,1). It is called strictly convex provided that the inequality (64) is strict for x≠y. Similarly, if -f: I→R is convex, then we say that f: I→R is concave.

Theorem A-1: Suppose f″ exists on (a,b). Then f is convex if and only if f″(x)≥0. And if f″(x)>0 on (a,b), then f is strictly convex on the interval.

B. Convex Sets

Let U be a subset of a linear space L. We say that U is convex if x,y∈U implies that $z = [\lambda x + (1-\lambda)y] \in U$ for all $\lambda \in [0, 1]$.

Theorem A-2: A set U⊆L is convex if and only if every convex combination of points of U lies in U.

We call the intersection of all convex sets containing a given set U the convex hull of U denoted by H(U).

Theorem A-3: For any U⊆L, the convex hull of U consists precisely of all convex combinations of elements of U.

Furthermore, for the convex hull, we have Carathéodory's theorem for convex sets.

Theorem A-4 (Carathéodory's Theorem): If U⊆L, and its convex hull of H(U) has dimension m, then for each z∈H(U), there exists m+1 points $x_0, x_1, \ldots x_m$ of U such that z is a convex combination of these points.

As discussed herein, a systematic approach to enhance the performance of suboptimal signal detection and estimation systems by adding suitable noise to the input signal has been developed (suboptimality may be due to inaccurate statistical models, model mismatch and system limitation, such as fixed decision threshold). This type of phenomenon is also known as stochastic resonance (SR) which occurs in some non-linear systems where the signals can be enhanced by adding suitable noise under certain conditions. Under the Bayesian and Neyman-Pearson frameworks, it has been determined whether or not a given detector is improvable by the addition of noise. If the detector is improvable, the pdf of the optimum noise to be added has been determined. See H. Chen, P. K. Varshney, J. H. Michels, and S. M. Kay, "Theory of the stochastic resonance effect in signal detection: Part 1–fixed detectors," IEEE Trans. on Signal Processing, vol. 55, no. 7, pp. 3172-3184, July, 2007 A number of cases including fixed and variable detectors were considered and significant performance enhancement was shown. H. Chen et al. supra; Chen et al. and H. Chen and P. K. Varshney, "Theory of the stochastic resonance effect in signal detection: Part II—variable detectors," IEEE Trans. on Signal Processing, October, 2008.

In accordance with an embodiment of the present invention, a more specific matter where SR noise is employed to enhance the detection of micro-calcifications in mammograms is also presented herein. A SR noise-based detection algorithm and a general detection enhancement framework to improve the performance of the suboptimal detectors has been developed. The dependence of the determination of the optimum SR noise is reduced on the knowledge of the pdfss of the object (lesion) and background (normal tissues) by employing iterative learning procedures. An iterative SR noise-based detection enhancement scheme with memory to improve the efficiency and robustness of the SR noise-based detection systems is also developed. Moreover, a more general SR noise-based detection enhancement framework is presented. Experiments and analyses are carried out to compare the performance of the presented SR noise-based detection algorithms and several other detection and classification methods. Detection algorithms considered/developed in the following experiments include the Gaussian background assumption-based detector, General Gaussian detector, General Gaussian detector-based iterative detector, Gaussian assumption-based dynamic clustering algorithm, iterative mode separation algorithm, Gaussian mixture model-based clustering method, and higher order statistics method based on local maxima detection and adaptive wavelet transform. The descriptions of these algorithms are presented and discussed in the following Examples presented below. The equations referenced in the following Examples start with Equation No. 1.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

EXPERIMENTAL DATA

The mammograms used herein are from the Digital Database for Screening Mammography (DDSM), and the Mammographic Image Analysis Society (MIAS) Mini-mammographic Database. However, the majority of the mammograms used in the experiments are from DDSM, and only few of them are from the MIAS database, so the experimental parameters, such as the processing window size, are determined mainly based on DDSM.

DDSM has 2620 cases available in 43 volumes. A case consists of between 6 and 10 mammograms, where the grey levels are quantized to 16 bits, and resolution of the images is 50 microns/pixel. The MIAS Database includes 330 mammograms with the resolution being 200 microns/pixel. The location and types (malignant or benign) of the mammogram lesions are identified by expert radiologists and used as the ground truth in our work. As discussed herein, the emphasis is on location detection based on the ground truth.

Three types of representative abnormal mammograms with micro-calcifications (clusters) including one having homogeneous background with a small number of isolated micro-calcifications were chosen, one having homogeneous background with a large number of micro-calcifications (clusters) and one having inhomogeneous background with a moderate number of micro-calcifications (clusters), respectively. These three types of mammograms cover a broad spectrum of mammogram micro-calcification (cluster) cases. Seventy five images selected from the three types of mammograms, 25 for each type, are employed to test the algorithms.

Micro-calcifications are very small, their sizes are in the range of 0.05-1.00 mm, and the average is 0.3 mm. Those smaller than 0.1 mm cannot be easily distinguished in the film-screen mammography from the high-frequency noise. The width of the majority of the micro-calcifications in these experiments is in the range between 0.25 and 0.5 mm. A micro-calcification cluster is considered to be a group of 3 to 5 or more micro-calcifications, 5 mm apart. The processing window size of 49 by 49 was chosen, which is based on experiments that were conducted as well as the characteristics and the size of the lesions. The experiments also indicated that the detection results were not very sensitive to the choice of window size provided that the window size was in the range between 31 and 61 when processing the data.

Since pixel by pixel detection was carried out, any isolated detected positive should not be considered to be a lesion due to the micro-calcification size mentioned above as well as the fact that the high-frequency noise may have serious influence on an individual pixel. Therefore, a micro-calcification (cluster) is declared to be detected only if at least 4 by 4 positively detected pixels are in a clump.

EXAMPLE 1

Problem Statement and Gaussian Assumption-Based Lesion Detection

This Example develops three lesion detectors based on Gaussian assumption. As discussed in more detail below, it will be shown that the detectors are all suboptimal detectors, suffering from model mismatch.

In this Example, the lesion detection problem from a statistical hypothesis testing point of view is introduced, and then three Gaussian assumption-based detectors for the lesion detection task are presented. It will be shown via experiments that the performance of these detectors is not satisfactory due to the large number of false alarms. This is due to model mismatch, and it results in suboptimality of the detectors.

Higher pixel intensity than the surrounding normal tissues distinguishes lesions from the normal structures in mammograms, which is one of the most important features of abnormal mammograms. The novel algorithms developed and presented herein perform the detection by exploring the pixel intensity information. This anomaly detection problem is dealt with by using statistical hypothesis testing methods. Formally, a choice should be made between one of the two hypotheses corresponding to the absence and presence of micro-calcifications on a pixel-by-pixel basis, $$H_0: y[m] = \omega[m]$$

$$H_1: y[m] = s[m] + \omega[m] \quad (1)$$

where m is the pixel index corresponding to the pixel observation under consideration, y[m] is the observed pixel intensity, larger than or equal to zero, s[m] is the lesion signal, and w[m] is the background noise that is assumed to obey Gaussian distribution with mean $\mu_b$ and variance $\sigma_b^2$. The noise is assumed to be additive, independently distributed and independent of the noise-free mammogram data. A processing window is employed with the pixel under consideration being at the center of the window. This window is employed to estimate the parameters of the detector by using the pixels included in it.

A. Gaussian Background Assumption-Based Detector (GBAD)

The Gaussian background assumption leads to linear and tractable solutions. The micro-calcifications, the signals of interest here, are brighter spots than the surrounding normal background tissues. So the micro-calcification is modeled as a signal with constant amplitude, and the lesion detection problem is to detect a DC signal in Gaussian noise, which we refer to as the Gaussian background assumption-based detector (GBAD). The lesion signal s[m] in Eq. (1) is, therefore, a constant intensity.

For this anomaly detection problem, the a priori probabilities of the background and lesion pixels are unavailable, so the Neyman-Pearson criterion for the detection task is employed. It is well known that under the Neyman-Pearson criterion, the optimal detector is a likelihood ratio test given as $$L(\bar{y}) = \frac{p(\bar{y}; H_1)}{p(\bar{y}; H_0)} \overset{\text{decide } H_1}{>} \gamma \quad (2)$$

where $\bar{y}$ is the observation vector, $p(\bar{y}; H_1)$ and $p(\bar{y}; H_0)$ are the pdfs under hypotheses $H_1$ and $H_0$, respectively. The threshold $\gamma$ is found from $$P_F = \int_{\{\bar{y}: L(\bar{y}) > \gamma\}} p(\bar{y} H_0) d\bar{y} = \beta \quad (3)$$

where $\beta$ is the desired value of the $P_F$.

Under the Gaussian background and DC signal assumptions, $p(\bar{y}; H_1)$ and $p(\bar{y}; H_0)$ all obey Gaussian distribution with the same variance $\sigma_b^2$, and the optimal test given in Eq.

(2) can be expressed in terms of the GBAD test statistic $T_{GBAD}(y)$ as follows $$T_{GBAD}(y) = y - \mu_b \overset{decide\ H_1}{\underset{>}{}} \gamma_1 \quad (4)$$

where y is the intensity of the pixel under consideration, and the threshold $\gamma_1$ is determined from the desired $P_F$ and the statistical parameters, i.e., mean and variance, of the pixels in the processing window.

To estimate the detector's parameters, an initial detection is first carried out in the processing window to perform a coarse detection, and the resulting detected negatives ($H_0$) and positives ($H_1$) are employed to estimate the parameters. Many methods, such as a local maxima filter or adaptive thresholding techniques, can perform the initial detection. Local maxima filter is employed in this work because the lesion pixels generally have a higher intensity than the surrounding normal background tissues.

For cancer diagnosis, the most serious mistake is to miss any lesions. To reduce the probability of miss ($P_M$), a "safer" initial detection is used and an attempt is made to exclude all the lesion pixels from the background. It can be realized by using a local maxima filter with appropriate window size and local threshold, permitting more pixels having relatively higher intensities in the local regions to be classified into the lesion part.

The detection results for GBAD are shown in FIGS. 13(b), 14(b) and 15(b), corresponding to three types of mammograms with micro-calcifications, as discussed further below. From the figures, it can be seen that the micro-calcifications are completely detected but with a higher $P_F$ than the desired value, 0.01 used in the experiments. At this point, it suffices to say that the performance of the detector is not satisfactory. A detailed discussion of the experimental results is postponed to Example 5, infra.

B. General Gaussian Detector (GGD)

Micro-calcifications, especially micro-calcification clusters, have a small size but generally do not have a constant intensity, so a Gaussian model as opposed to a constant signal model is proposed in this section to be a more reasonable model to represent the signal part. Thus, the problem can be considered to be the problem of detection of Gaussian signals in Gaussian noise. This detector is referred to as the general Gaussian detector (GGD). The lesion signal s[m] in Eq. (1) under this assumption obeys Gaussian distribution, i.e., s[m] $\sim N(\mu_s, \sigma_s^2)$.

The detected positive pixels (corresponding to lesions) and negative pixels (corresponding to the background) in the initial detection are employed to coarsely estimate the means and variances of the lesion and background pixel intensity pdfs. Under the GGD assumption, $p(\bar{y}; H_1)$ and $p(\bar{y}; H_0)$ in Eq. (2) obey Gaussian distribution but with different variances, and the optimal test is still the likelihood ratio test given in Eq. (2). The optimum test can be expressed in terms of the GGD test statistic $T_{GGD}(y)$ as follows $$T_{GGD}(y) = \frac{\sigma_s^2}{\sigma_b^2}(y - \mu_b)^2 + 2\mu_s(y - \mu_b) \overset{decide\ H_1}{\underset{>}{}} \gamma_2 \quad (5)$$

where the threshold $\gamma_2$ is determined from the desired $P_F$. The statistical parameters, namely the means and the variances, of the initially detected positive and negative pixels can be estimated using the processing window with the pixel under consideration at the center of the window.

It can be seen that when $\sigma_s^2 \to 0$, the first term on the right side of Eq. (5) tends to zero, and Eq. (5) reduces to a form similar to Eq. (4), which corresponds to s[m] being a constant signal. It is also noticed that Eq. (5) is a detector with two thresholds because the test statistic is quadratic. Due to the nature of the abnormal mammograms, i.e., lesion pixels have intensities that are generally higher than the surrounding normal background tissues and the probability of the intensities of lesion pixels falling below the lower threshold is extremely small, thus, only the higher threshold is employed to classify the mammogram pixels into background and lesions. Therefore, the higher threshold of the test in Eq. (5) is used herein for the detection task.

The detection results for GGD are shown in FIGS. 13(c), 14(c) and 15(c), as discussed further in Example 5, infra, where all the micro-calcifications are discovered by GGD, with less false positives compared with the GBAD.

C. GGD-Based Iterative Detector (GGD_ID)

Encouraged by the improvement achieved by the GGD over GBAD, an iterative method is proposed to further improve the performance of GGD by increasingly improving the estimation of statistical parameters in an iterative manner.

At each step of the iteration, the GGD is designed with the parameters, $\mu_s$, $\mu_b$, $\sigma_s^2$ and $\sigma_b^2$, corresponding to the background and micro-calcifications, estimated from the detection result in the preceding iteration as opposed to keeping them fixed during all iterations, which results in different thresholds at each iteration.

The procedure of the iterative detection algorithm is described as follows:

Initialization: Initial detection using the coarse detector described in Example 1.A.

Step 1: Means and variances of the detected positive (lesion) and negative (background) pixels are calculated.

Step 2: Detection is performed using the GGD (Eq. (5)) with the desired $P_F$ and the updated parameters, $\mu_s$, $\mu_b$, $\sigma_s^2$ and $\sigma_b^2$, calculated in Step 1. If there are no differences in the detected positives and negatives between two successive detections, terminate the algorithm, else go to Step 1.

The presented GGD_ID algorithm is similar in spirit to Gaussian model-based dynamic clustering (GMDC), in which both background and lesions are assumed to obey Gaussian distributions, and the detection (or clustering) and parameter updating are performed in an iterative manner. The difference is that the method presented here incorporates an additional constraint in terms of the desired value of $P_F$. The reason $P_F$ is included in the algorithm is that at each step of the iteration, some detected negative pixels have intensities much larger than the mean of the detected background pixels and are close to that of the detected lesion pixels. In other words, some pixels have a non-negligible and, in fact, fairly high probability to belong to the lesion part. Since it is preferable that no lesions be missed, these pixels are classified into the lesion part by the desired $P_F$ value, such as the value 0.01 used herein. It is discussed in Example 5, infra, that the iterative detection method presented here performs better than the GMDC.

The detection results for this detector are shown in FIGS. 13(d), 14(d) and 15(d), and discussed in Example 5, infra, where the GGD is employed iteratively four times on the mammograms. Experiments show that the method generally converges within 5 iterations.

D. Model Mismatch Analysis

From the experimental results, it can be seen that the detection performance has improved with the melioration of the detection schemes, but the final results are still not satisfactory as seen via inexact lesion contours and large number of false positives. The resulting diagnosis may result in additional testing and biopsies for spots on mammograms that finally turn out to be harmless, which is a weakness many CAD systems exhibit currently.

One major reason for the unsatisfactory detection is that the Gaussian assumption does not accurately model the background distribution and the resulting test including the detection threshold is not optimal. A more accurate model for the background, heavy-tailed symmetric α stable (SαS) distribution, was proposed in Banerje et al., which has also been verified by the experiments described herein. Amit Banerje and Rama Chellappa, "Tumor detection in digital mammograms," in Proc. International Conference on Image Processing (ICIP'00), vol. 3, pp. 432-435, Vancouver, BC, Canada, 2000.

Figure 12:
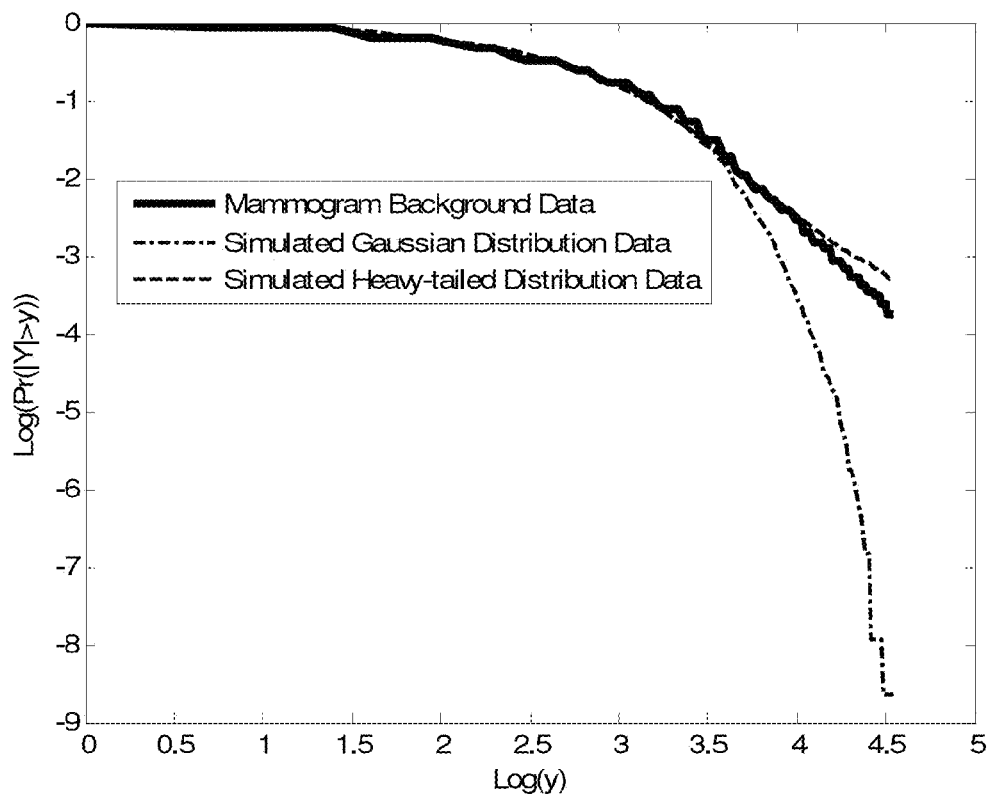
FIG. 12 is a schematic of APD plots of the real-world mammogram background data, simulated Gaussian distribution and heavy tailed SαS distribution data on a log-log scale, in accordance with an embodiment of the present invention.

For verification, the following is shown in FIG. 12—the amplitude probability distribution (APD) plots of real-world mammogram background data of a mammogram from the MIAS Mini-mammographic Database, and simulated Gaussian distribution and heavy-tailed SαS distribution data on a log-log scale (showing that the mammogram pixel intensities obey heavy-tailed SαS distribution more closely). Plotting APD is a commonly used method to test impulsive noise. It is defined as the probability that the noise amplitude is above some threshold. It can be seen from FIG. 12 that for small amplitudes, the simulated heavy-tailed distribution and Gaussian distribution provide good fits to the mammogram data. At larger amplitudes (i.e., at the tails), the simulated heavy-tailed SαS distribution is shown to be a better fit than the Gaussian one. In addition, the plots of the mammogram data and the simulated heavy-tailed SαS data decay linearly with a constant slope compared with that of the Gaussian data. These two observations indicate that the heavy-tailed SαS distribution is a better model than the Gaussian model for the background pixel intensities of a digital mammogram. Hence, there exists empirical support for the existence of the SαS noise distribution in mammogram background (as opposed to the Gaussian distribution). Theoretical analysis and more detailed discussion on this can be found in Banerje et al., supra.

One approach to the design of the optimal lesion detector is to derive the optimal test under the Neyman-Pearson formulation when the background is modeled as the SαS distribution. However, the difficulties in learning the parameters of the SαS distribution from the real-world data as well as the off-line integration when calculating the detection threshold constrains the practical application of the optimal SαS-based detectors. In the following Examples, an alternate approach in accordance with an embodiment of the present invention is investigated, namely the application of SR noise, to the lesion detection problem. The suboptimal detectors designed based on the Gaussian noise background assumption will continue to be used. Admittedly there is a model mismatch. In an attempt to overcome the deterioration in the detector performance, SR noise at the input will be added to the detector. It will be seen that the SR noise-based detector yields significant performance enhancement and is easy to implement.

EXAMPLE 2

Optimum SR Noise-Enhanced Signal Detection

This Example presents the main results of work on SR noise-enhanced signal detection under Neyman-Pearson criterion, where the optimum form of the SR noise is determined.

One of the main goals of an embodiment of the present invention is to develop SR noise-enhanced detection methods for lesion detection in mammograms. First, the fundamental results on SR noise-enhanced signal detection is presented in this Example.

A binary statistical decision problem is considered. Similar to the statement in Example 1, a choice between the two hypotheses should be made $$\begin{cases} H_0: p_{\bar{y}}(\bar{y}; H_0) = p_0(\bar{y}) \\ H_1: p_{\bar{y}}(\bar{y}; H_1) = p_1(\bar{y}) \end{cases} \quad (6)$$

where $\bar{y}$ is an N-dimensional data vector, i.e., $\bar{y} \in R^N$. $p_0(\bar{y})$ and $p_1(\bar{y})$ are the pdfs of $\bar{y}$ under $H_0$ (background) and $H_1$ (lesion) hypotheses, respectively. Pixel by pixel detection is only considered herein, so $\bar{y}$ reduces to a scalar y. During the decision process, a test is necessary to choose between the two hypotheses, which can be completely characterized by a critical function, or decision function, $\phi(\bar{y})$, $0 \leq \phi(\bar{y}) \leq 1$, and $$\phi(\bar{y}) = \begin{cases} 1: T(\bar{y}) > \gamma \\ \beta: T(\bar{y}) = \gamma \\ 0: T(\bar{y}) < \gamma \end{cases} \quad (7)$$

where T is the test statistic and a function of $\bar{y}$. $\gamma$ is the threshold, and $0 \leq \beta \leq 1$ is a suitable number.

The detection performance of this test can be evaluated in terms of $P_D$ and $P_F$, $$P_D^{\bar{y}} = \int_{R^N} \phi(\bar{y}) p_1(\bar{y}) d\bar{y} \quad (8)$$

$$P_F^{\bar{y}} = \int_{R^N} \phi(\bar{y}) p_0(\bar{y}) d\bar{y} \quad (9)$$

where $P_D^{\bar{y}}$ and $P_F^{\bar{y}}$ represent the $P_D$ and $P_F$ of the detector based on the input $\bar{y}$, respectively.

The SR noise-based detection enhancement scheme is to add an appropriate noise $\bar{n}$ to the original data $\bar{y}$, which yields a new data vector $\bar{z}$ $$\bar{z} = \bar{y} + \bar{n} \quad (10)$$

where $\bar{n}$ is either a random vector with pdf $p_{\bar{n}}(.)$ or a nonrandom signal.

The binary hypotheses testing problem for this new observed data can be expressed as $$\begin{cases} H_0: p_{\bar{z}}(\bar{z}; H_0) = p_0(\bar{z}) = \int_{R^N} p_0(\bar{y}) p_{\bar{n}}(\bar{z} - \bar{y}) d\bar{y} \\ H_1: p_{\bar{z}}(\bar{z}; H_1) = p_1(\bar{z}) = \int_{R^N} p_1(\bar{y}) p_{\bar{n}}(\bar{z} - \bar{y}) d\bar{y} \end{cases} \quad (11)$$

The SR noise-enhanced fixed detectors are considered herein whose parameters, such as the thresholds, are unchanged before and after adding the SR noise, so the critical function $\phi$ of $\bar{z}$ is the same as that of $\bar{y}$. Therefore, $$P_D^{\bar{z}} = \int_{R^N} \phi(\bar{z})p_1(\bar{z})d\bar{z} \qquad (12)$$

$$= \int_{R^N} p_{\bar{n}}(\bar{y})\left(\int_{R^N} \phi(\bar{z})p_1(\bar{z}-\bar{y})d\bar{z}\right)d\bar{y}$$

$$= \int_{R^N} F_1(\bar{y})p_{\bar{n}}(\bar{y})d\bar{y}$$

And similarly $$P_F^{\bar{z}} = \int_{R^N} \phi(\bar{z})p_0(\bar{z})d\bar{z} = \int_{R^N} F_0(\bar{y})p_{\bar{n}}(\bar{y})d\bar{y} \qquad (13)$$

where $$F_i(\bar{y}) = \int_{R^N} \phi(\bar{z})p_i(\bar{z}-\bar{y})d\bar{y},$$

corresponds to hypothesis $H_i$.

The sufficient condition for improvability of detection via SR noise is given in Theorem 1.

Theorem 1: If $J(P_F^{\bar{y}}) > P_D^{\bar{y}}$ or $J''(P_F^{\bar{y}}) > 0$ when $J(t)$ is second-order continuously differentiable around $P_F^{\bar{y}}$, then there exists at least one noise process $\bar{n}$ with pdf $p_{\bar{n}}(.)$ that can improve the detection performance, where $J(t)$ is defined as the maximum value of $f_1$ given $f_0$, i.e., $J(t)=\sup(f_1: f_0=t)$. $f_0$ and $f_1$ are the given values of $F_0$ and $F_1$, respectively.

Theorem 2 determines the form of the optimum SR noise when the detector is improvable.

Theorem 2: To maximize $P_D^{\bar{z}}$, under the constraint that $P_F^{\bar{z}} \leq P_F^{\bar{y}}$, the optimum noise can be expressed as $p_{\bar{n}}^{opt}(\bar{n})=\lambda\delta(\bar{n}-\bar{n}_1)+(1-\lambda)\delta(\bar{n}-\bar{n}_2)$, where $\lambda$ and $1-\lambda$ are the occurrence probabilities of the suitable N-dimensional vectors $\bar{n}_1$ and $\bar{n}_2$, $0 \leq \lambda \leq 1$.

The approach to determine $\lambda$, $\bar{n}_1$ and $\bar{n}_2$ is discussed in detail in H. Chen, P. K. Varshney, J. H. Michels, and S. M. Kay, "Theory of the stochastic resonance effect in signal detection: Part 1—fixed detectors," IEEE Trans. on Signal Processing, vol. 55, no. 7, pp. 3172-3184, July, 2007. They can be determined in practice using numerical methods. Since the optimum SR noise is a randomization of two deterministic vectors, it is called the "Two peak SR noise" herein.

The advantage of a SR noise-enhanced fixed detector is that the parameters, such as the threshold, of the original detector do not need to be changed, yet better detection performance is expected. In other words, model mismatch can be handled fairly easily by using this approach. However, to obtain the optimum SR noise, full knowledge of the pdfs under the two hypotheses is required, which in real-world applications is generally not available. In the next two Examples, the issue of how to find the suitable SR noise for enhancing a suboptimal lesion detector when the knowledge of the pdfs is incomplete is discussed.

EXAMPLE 3

SR Noise-Enhanced Gaussian Assumption-Based Detection

This Example relates to the development of a SR noise-based detection algorithm for lesion detection that attempts to improve the suboptimal detectors discussed in Example 1. An interative detection scheme involving the use of SR noise with memory is also presented.

In this Example, the SR noise-enhanced detection approach is employed for finding lesions and enhancing the previously discussed suboptimal detectors based on the Gaussian assumption. Pixel-by-pixel detection was performed. The suboptimal detectors to be improved result from the model mismatch and the lack of information about the mammogram statistics. These detectors are excellent candidates for the application of the SR noise-enhanced detection scheme.

The basic idea of the SR noise-enhanced detection is to obtain the optimum additive SR noise based on the knowledge of the pdfs of the lesion and the background signals. Since these pdfs are not known, they need to be estimated from the given mammogram itself. The mammogram is modified with the optimum additive SR noise determined using, the estimated pdf, and then the original suboptimal detector performs the detection. Two SR noise-based schemes are presented in this Example for improving lesion detection.

A. Two Peak SR Noise-Enhanced Gaussian Background Assumption-Based Detection (2SR-GBAD)

In this algorithm, an attempt is made to reduce the dependence of the SR noise determination on the knowledge of the true pdfs and increasingly enhance the suboptimal detectors through an iterative procedure.

The SR noise is first used to enhance the GBAD discussed in Example 1. To achieve this goal, the coarse detection of the lesion and background was performed using the local maxima filter mentioned in Example 1A. The detection threshold is calculated for the GBAD, which is suboptimum due to model mismatch. Then, the probability densities under $H_1$ and $H_0$ are obtained using the kernel density estimation method based on the detected positives and negatives. Kinosuke Fukunaga, Introduction to Statistical Pattern Recognition (second edition), Academic Press, September, 1990. The parameters of the SR noise are calculated from the suboptimum threshold and the estimated densities. The SR noise is added to the original mammogram. Detection is performed on the SR noise-modified data using the original detector. This procedure is repeated in an iterative manner until the difference between two successive detection results is very small (There could be many methods to define and evaluate the difference. In these experiments, the difference is defined as the ratio of the number of differently labeled pixels in two successive detections to the total number of pixels in the mammogram. The labeled pixel here means a pixel classified as a positive (lesion) pixel or a negative (background) pixel. The iterative process is terminated when the ratio is smaller than a desired value.).

The procedure of the 2SR-GBAD detection algorithm is described as follows:

Initialization: Initial detection using the coarse detector described in Example 1A.

Step 1: Mean $\mu_b$ and variance $\sigma_b^2$ of the background are estimated, based on the detected negative pixels. The detection threshold is updated based on the desired $P_F$ as well as $\mu_b$ and $\sigma_b^2$ using Eq. (3), where it is assumed that the background obeys Gaussian distribution (see GBAD in Example 1A).

Step 2: The pixels are detected with the updated threshold found in Step 1. The resulting detected positive and negative pixels are employed for estimating probability densities under the two hypotheses using the kernel density estimation method.

Step 3: The updated threshold in Step 1 and the newly estimated probability densities in Step 2 are used to determine the SR noise with the method mentioned in Example 2.

Step 4: The mammogram data is modified by adding to the original pixel intensities the SR noise determined in Step 3.
Step 5: Detection is performed with the detector updated in Step 1 using the modified data from Step 4. If the difference between two successive detection results is very small, terminate the algorithm else go to Step 1.

According to the experiments, a good initialization can be generated by schemes such as a maxima filter with an appropriate window size and threshold, such that satisfactory detection can still be obtained even when the threshold update procedure in Step 1 is not performed during the iterations. In other words, the critical function can remain fixed throughout the iterations if the initial detection is good enough. The threshold updating can also be performed every several iterations to improve the computation speed.

In a similar manner, the above procedure can be used to design the SR noise enhanced GGD test, i.e., 2SR GGD where the means, $\mu_s$ and $\mu_b$, and variances, $\sigma_s^2$ and $\sigma_b^2$, of the detected positives and negatives as well as the desired $P_F$ are used together to update the threshold in Step 1. The rest of the four steps of 2SR-GGD are the same as those of 2SR-GBAD. Since GGD is a more accurate model for abnormal mammograms, which can be seen in the comparison between the detection results of GBAD and GGD, 2SR-GGD yields better performance than 2SR-GBAD, according to the experiments. The 2SR-GGD method also shows improvement over GGD detection. What's more, the presented algorithm generally needs fewer iterations than GGD_ID discussed in Example 1C to reach similar detection results. Also, the final results of the presented algorithm are better than GGD_ID.

B. Two Peak SR Noise-Enhanced Gaussian Assumption-Based Detection with Memory (2SR-GBAD-M)

The experiments show the improved performance of the 2SR-GBAD-M algorithm. In this section, its efficiency and robustness is further improved by introducing memory in the detection enhancement scheme.

To find the optimum SR noise, the exact knowledge of the probability distribution under the two hypotheses and the determination of the solution for a set of equations are required. However, in real-world applications, due to incomplete information about the distribution, limitations on the accuracy when solving the equations and various contents of mammograms, high efficiency and robustness of the SR noise-enhanced detection system may not be achievable using the SR noise-based enhancement procedure only once. Multiple applications of the procedure may yield further enhancement of detection performance. Therefore, suitably arranged multiple two peak SR noises are applied multiple times to increase the efficiency and robustness of the detection system, which is referred to as 2SR-GBAD-M.

Formally, for the SR noise-based scheme with memory, there is $$\bar{z} = \bar{y} + \bar{n}^* \quad (14).$$

where $\bar{n}^*$ represents multiple-peak SR noises instead of a single two peak SR noise added to the original mammogram data in Step 4 of the algorithm presented in Example 3A, and $$p_{\bar{n}} = \sum_{k=1}^{r} w_k p_{\bar{n}_k} \quad (15)$$

where $w_k$ is the weight or probability of occurrence of the $k^{th}$ two-peak SR noise, $0 \leq w_k \leq 1$ and $$\sum_{k=1}^{r} w_k = 1.$$

r is the number of the two-peak SR noises which in our current work equals the number of iterations already run plus 1 (i.e., the SR noise determined from the estimated probability mass function (PMF) and the updated threshold at current iteration is also included, where PMF is used as the specific form of the probability distribution for discrete digital mammogram data), and $$p_{\bar{n}_k}(\bar{n}) = \lambda_k \delta(\bar{n} - \bar{n}_{1k}) + (1 - \lambda_k) \delta(\bar{n} - \bar{n}_{2k}) \quad (16)$$

Of course, we can change the memory size by using different values of r, but in any case the latest r two-peak SR noises should be employed. When r=1, a single two-peak noise is used, and the scheme reduces to the scheme without memory.

At each step of iteration, a larger weight, i.e., higher probability is allocated to the SR noise calculated from the currently estimated PMFs, and the weights for the rest of the SR noises are inversely proportional to the distances between their corresponding PMFs and the currently estimated ones. The distance D between the PMFs obtained during the $1^{th}$ iteration and the latest estimated PMFs is defined as $$D_l = \sum_{i=0}^{255} [|PMF_{lH_0}(i) - PMF_{eH_0}(i)| + |PMF_{lH_1}(i) - PMF_{eH_1}(i)|] \quad (17)$$

where $PMF_{lH_j}$ denotes the PMF under hypothesis $H_j$ obtained during the $l^{th}$ iteration, and j=0,1. $PMF_{eH_j}$ is the estimated PMF under hypothesis $H_j$ obtained at the current iteration. The summation is over all possible image intensity values. This approach to incorporate memory has resulted in encouraging results as will be seen in the Example 5, infra. The detection results of the two peak SR noise enhanced GBAD tests with memory are shown in FIGS. 13(f), 14(f) and 15(f), from which the Gaussian assumption-based detection can be seen suffering from model mismatch is improved through the addition of SR noise. Experiments also show that 2SR-GGD-M yields better performance than 2SR-GBAD-M. A more general SR noise-based detection enhancement framework based on the work in this Example is presented in Example 4, infra.

EXAMPLE 4

SR Noise-Based Detection Enhancement Framework

A SR noise-based detection enhancement method was presented in Example 3 to reduce the model mismatch resulting from the Gaussian assumption. When models other than Gaussian models are used to fit data, there may still exist model mismatches, resulting in detector performance degradation, and SR noise may enhance the detector performance. In this Example, the SR noise-based detection scheme is extended and a more general SR noise-based detection enhancement framework is presented. This framework provides much more flexibility and higher efficiency. The detectors (or classifiers) which are controlled are the ones that are considered herein, i.e., their thresholds can be changed.

The framework is developed by modifying the first two steps of the detection procedure presented in Example 3 and is shown as follows.

Initialization: Initial detection.

Step 1: Probability density estimates are obtained under the two hypotheses using the detected positive (lesion) and negative (background) pixels. The detection threshold (or the classifier) is updated according to the estimated probability density information.

Step 2: The pixels are classified (or detected) with the updated threshold or the classifier in Step 1. The resulting detected positive and negative pixels are employed for estimating probability densities under the two hypotheses.

Step 3: The updated threshold or classifier in Step 1 and the newly estimated probability densities in Step 2 are used to determine the SR noise with the method mentioned in Example 2.

Step 4: The mammogram data is modified by adding SR noise to the original pixel intensities.

Step 5: Detection is performed with the detector or classifier updated in Step 1 using the modified data from Step 4. If the difference between two successive detection results is very small, terminate the algorithm else go to Step 1.

To improve the efficiency and robustness of the detection framework, the two peak SR noise scheme with memory, which yields multi peak SR noise, can also be used in Step 4.

It is noted that no specific constraints are put on the initialization, threshold or classifier updating and pdf estimation methods used in this framework. Any reasonable approaches could be employed. As shown herein, the ability of the framework is illustrated by considering different algorithms for threshold or classifier updating and pdf estimation. For initialization, the maxima filter discussed in Example 1A is still used. For threshold or classifier updating, one may use the methods that can converge when there is no SR noise added, such as GMDC and iterative mode separation (IMS) algorithms. IMS is an unsupervised learning pattern classification approach, which employs kernel density estimation technique to determine the pdf and performs clustering in an iterative manner. For pdf estimation, one may use non-parametric methods, such as kernel density estimation, k-nearest neighbor density estimation and Bootstrap methods, etc., because it is desirable to reduce the model mismatch during the pdf estimation as well as the dependence of the framework on modeling, and to make the framework more generally usable. Efron, B. and R. J. Tibshirani, An Introduction to the Bootstrap, Chapman & Hall, 1993; José I. De la Rosa and Gilles A. Fleury, "Bootstrap Methods for a Measurement Estimation Problem," IEEE Trans. on Instrumentation and Measurement, vol. 55, no. 3, pp. 820-827, June, 2006. In accordance with an embodiment of the present invention, for performance comparison, the kernel density estimation approach and threshold update using Eq. (18) is employed, same as those used in IMS. It is observed in Example 5 that the SR noise-based method can further improve the performance of IMS. The threshold updating is carried out by using $$P_0 p_0(y^*) = P_1 p_1(y^*) \tag{18}$$

where $y^*$ is the updated detection threshold during the current iteration. $P_0$ and $P_1$ are the a priori probabilities of the detected negatives and positives, which can be estimated by $\hat{P}_i = n_i/n$, where $n_i$ is the number of negatively detected pixels when $i=0$ and positively detected pixels when $i=1$, and n is the total number of pixels in the mammogram. This generates a sub-optimal detector because the threshold is determined from the coarsely estimated a priori probabilities and pdfs by using the plug-in rule. Geoffrey Mclachlan and David Peel, Finite Mixture Models, A Wiley-Interscience Publication, 2, Oct. 2000. Experimental results show that the SR noise-based algorithm presented herein generally needs fewer number of iterations than IMS to reach similar detection results. Also, the final results of SR noise-based algorithm are better than IMS, where the final results are attained when the difference between two successive detection results is very small. In addition, given a good initialization, satisfactory detection can still be obtained even when the threshold or classifier update procedure in Step 1 is not performed during the iterations.

It can be seen that the above iterative procedure includes a scheme for pdf estimation, but in the current detection (or clustering) application, the estimated pdfs are not of interest as an end in themselves. Instead, the detection results are the focus here which, of course, depend on the estimate. At the same time, an accurate pdf estimate can also be obtained from an accurate detection. So, the detection results are used in this paper as an alternative way to evaluate the performance of the pdf estimation algorithm. For comparison, a Gaussian mixture modeling (GMM)-based clustering method which performs the detection based on the GMM fitted pdf is employed with the detection results shown in Example 5, infra.

EXAMPLE 5

Performance Comparison and Analysis

This Example relates to the presentation of experimental results and the performance evaluation of several lesion detection and classification algorithms. The algorithms that are compared and analyzed include GBAD, GGD and GGD_ID discussed in Example 1, GADC, 2SR-GBAD-M, IMS, GMM-based clustering method, high order statistics method based on local maxima detection and adaptive wavelet transform (HOSLW) and the SR noise-based detection enhancement framework using a procedure similar to IMS, i.e., SR_IMS.

The first four algorithms are based on the Gaussian distribution assumption and are parametric approaches. GMM is a semi-parametric technique for pdf estimation, in which the superposition of a number of parametric densities, e.g., Gaussian distribution, are used to approximate the underlying pdf. It offers a useful compromise between the non-parametric methods mentioned in Example 4, and the parametric estimation methods, such as those mentioned above. For the clustering application, the GMM given in Eq. (19) is first fit by using the Expectation-maximization algorithm $$f(y) = \sum_{i=1}^{g} P_i f_i(y) \tag{19}$$

where f(y) is the density of the observation y, and $f_i(y)$ are the component densities of the mixture. g is the number of components, which can be preset or automatically determined according to the data statistics. As discussed herein, we set g=2 to facilitate two-class clustering. $P_i$ are the mixing proportions or weights, $0 \leq P_i \leq 1$ (i=1, ..., g) and $$\sum_{i=1}^{g} P_i = 1.$$

The clustering is performed by using the plug-in rule given in Eq. (20) based on the Bayes rule $$R(y) = i \text{ if } \hat{P}_i \hat{f}_i(y) \geq \hat{P}_j \hat{f}_j(y) \tag{20}$$

for j=1, ..., g, where R(y)=i denotes that the allocation rule R(y) assigns the observation y to the $i^{th}$ component of the mixture model. $\hat{P}_i$ and $\hat{f}_i(y)$ are the fitted values of $P_i$ and $f_i(y)$, respectively.

The HOSLW algorithm is proved to have superior performance compared with other existing methods in terms of efficiency and reliability. In this method, local maxima of the mammogram are determined as the lesion candidates, and the adaptive wavelet transform is employed to generate subbands which permit the rank of these maxima in the subband mammogram using a higher order statistical test for lesion detection.

For fairness, the same initial detection is used for the algorithms compared in the experiments. In 2SR-GBAD-M and SR_IMS, the weights of the two peak SR noise calculated from the currently estimated pdfs are set to be 0.5.

Experiments have been carried out using 75 images, and the results of five detection/classification algorithms are presented in Table 2, infra, in terms of true-positive fraction (TP) and false positives per image (FPI), where TP is defined as the ratio of the number of the true positive marks to the number of lesions and FPI is defined as the average number of false positives per image. In these experiments, if a detected positive area has more than 50% overlap with the ground truth area, the detected area is considered to be a TP lesion. Otherwise, it is considered to be a false positive. This is the same definition as used in Heng-Da Cheng, Yui Man Lui, and Rita I. Freimanis, "A novel approach to micro-calcification detection using fuzzy logic technique," IEEE Trans. on Medical Imaging, vol. 17, no. 3, June 1998.

Figure 13:
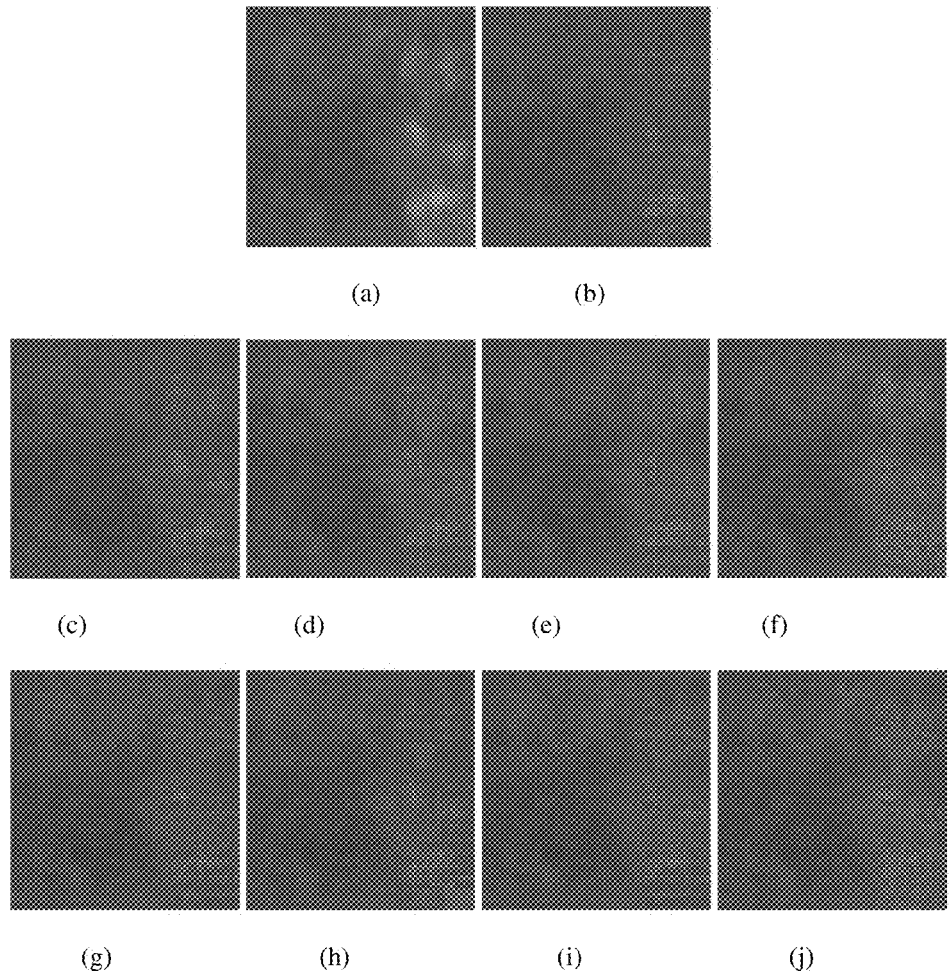
FIG. 13 shows the detection results for abnormal mammogram type 1 using novel algorithms in accordance with an embodiment of the present invention.
Figure 14:
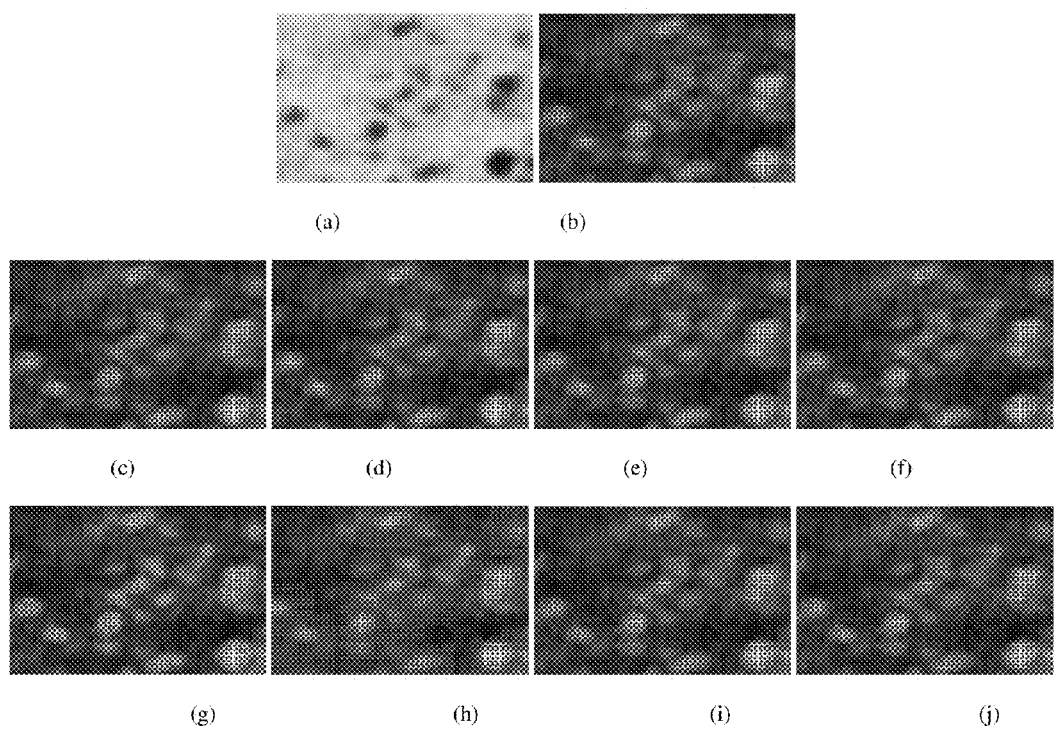
FIG. 14 shows the detection results for abnormal mammogram type 2 using novel algorithms in accordance with an embodiment of the present invention.
Figure 15:
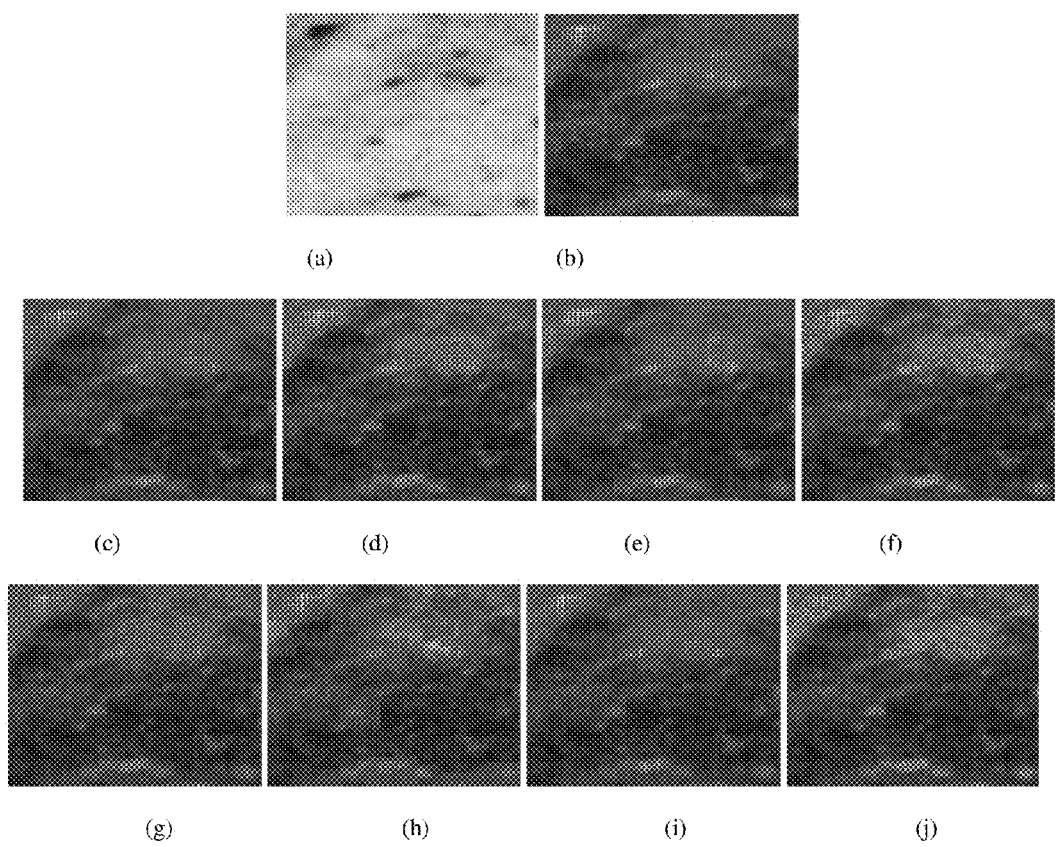
FIG. 15 shows the detection results for abnormal mammogram type 3 using novel algorithms in accordance with an embodiment of the present invention.

The qualitative evaluation of these algorithms are presented first. FIGS. 13, 14 and 15 show the experimental results for the three ROIs cut from three representative mammograms, where the detected positive pixels are labeled with small dots. In brief, FIG. 13 shows original abnormal mammogram and the detection results (Abnormal mammogram type I: homogeneous background with small number of isolated micro-calcifications). (a) Original mammogram with micro-calcifications; (b) GBAD; (c) GGD; (d) GGD_ID; (e) GADC; (f) 2SR-GBAD-M; (g) IMS; (h) HOSLW; (i) GMM-based detection; (j) SR_IMS. FIG. 14 shows original abnormal mammogram and the detection results (Abnormal mammogram type 2: homogeneous background with large number of micro-calcifications (clusters)). (a) Original mammogram with micro-calcifications; (b) GBAD; (c) GGD; (d) GGD_ID; (e) GADC; (f) 2SR-GBAD-M; (g) IMS; (h) HOSLW; (i) GMM-based detection; (j) SR_IMS. FIG. 15 shows original abnormal mammogram and the detection results (Abnormal mammogram type 3: inhomogeneous background with moderate number of micro-calcifications (clusters)). (a) Original mammogram with micro-calcifications; (b) GBAD; (c) GGD; (d) GGD_ID; (e) GADC; (f) 2SR-GAD-M; (g) IMS; (h) HOSLW; (i) GMM-based detection; (j) SR_IMS. For each Figure, the detected positive pixels are labeled with dots.

In the experiment shown in FIG. 13, a fixed threshold is employed in the 2SR-GBAD-M and SR_IMS algorithms throughout the iterations. The complexity of the mammogram used in these experiments is the lowest compared with the other two to be discussed next. From the figures, it can be seen that the GBAD and GGD methods find all the lesions, but at the same time generate many false alarms (see 13(b) and 13(c)). GGD_D (13(d)) is a more robust method. It improves the detection of GGD and performs better than the GADC and IMS methods shown in 13(e) and 13(g), but it still fails to reduce the false positives satisfactorily. The advantage of the GADC is that it converges quickly, generally in no more than 8 iterations in these experiments, while IMS converge to local extrema. HOSLW method (13(h)) can find the lesions efficiently, but it fails to determine lesion shape which plays a very important role in discriminating the benign tumors from the malignant ones. Moreover, its detection performance depends on how accurately the number of lesion pixels can be estimated, which is generally not available or known in real-world cases. These detectors suffer from model mismatch and parameter suboptimality resulting in suboptimum detection threshold, and their performances are degraded. The GMM-based detector finds all the lesions but still does not avoid the high $P_F$ (see 2(i)), which is due to the inaccuracy when GMM is used to fit the mammogram data. In contrast, the presented 2SR-GBAD-M and SR_IMS algorithms yield good detection results in terms of lesion localization, lesion contour exploration and $P_F$ reduction (see 13(f) and 13(j)), which demonstrates the capability of the SR noise-based method for enhancing the detectors with model mismatch and parameter suboptimality. Comparing 13(f) and 13(j), it can be seen that SR_IMS performs a little better than 2SR-GBAD-M in reducing false alarms and determining lesion boundaries.

FIG. 14 shows a more complex case, where both isolated micro-calcifications and crowded clusters exist and the number of lesions is large. It can be seen that still the 2SR-GBAD-M and SR_IMS algorithms yield better detections with clearer lesion contours and less false positives (see 14(f) and 14(j)). Compared with GBAD and GGD in 14(b) and 14(c), GGD_ID and GADC method shown in 14(d) and 14(e) perform better but still with high $P_F$'s. IMS fails to find some lesions (see 14(g)). HOSLW (14(h)) does not provide much useful information about the lesion positions in this crowded micro-calcifications (clusters) case. This is because its detection operation is performed in subband images which have a quarter of the size of the original mammogram, so the area of the detected positives will be four times of those in the subband images when the detection result is shown in the original mammogram. When the micro-calcifications (clusters) are close to each other, their boundaries and locations are hard to determine. GMM performs better than the rest of the methods (except for 14(f) and 14(j)), but still generates many false alarms.

FIG. 15 is the most complex case, where the background distribution is inhomogeneous and some background pixels have their intensities approaching the lesion pixels. It is hard to model the background using just a univariate probability distribution. Finite mixture models may be a choice, but to determine the model type and parameters is also a challenging task. Also, their performance could be deteriorated by the non-stationary nature of the images. Therefore, model mismatch in this type of images is more serious and unavoidable. In this experiment, univariate Gaussian distribution is still used to model the pixel intensity distributions of the background and lesion, respectively, through which the model mismatch is simulated. From FIG. 15, it can be seen that the performance of all the detectors degrades to some extent with higher $P_F$ and lower $P_D$ values as well as more imprecise lesion contours compared with the previous two cases. But the presented 2SR-GBAD-M and SR_IMS algorithms (see FIG. 15(f) and FIG. 15(j)) still stand out with better detection results, which again demonstrate their efficiency in reducing the negative influences of model mismatch and suboptimum parameters.

TABLE 2

DETECTION PERFORMANCE OF FIVE ALGORITHMS

| RESULTS | METHODS | GADC | IMS | 2SR-G | SR_I | HO |
|---|---|---|---|---|---|---|
| TP | Range | [0.61, 1] | [0.58, 1] | [0.80, 1] | [0.81, 1] | [0.81, 1] |
|  | Mean | 0.89 | 0.90 | 0.93 | 0.94 | 0.94 |
|  | Standard deviation | 0.25 | 0.28 | 0.12 | 0.11 | 0.11 |
| FPI | Range | [0, 20] | [0, 17] | [0, 9] | [0, 7] | [0, 14] |
|  | Mean | 8.16 | 7.89 | 4.91 | 3.12 | 5.22 |
|  | Standard deviation | 6.18 | 7.08 | 3.94 | 2.95 | 4.82 |

2SR-G: 2SR-GBAD-M; SR_I: SR_IMS; HO: HOLSW.

Next, the quantitative measurement of the algorithms is shown. Three methods are selected to compare with 2SR-GBAD-M and SR_IMS, and the results are presented in Table 2. The reason GADC and IMS were chosen is that they are all classical pattern classification methods and also based on iterative procedures, like 2SR-GBAD-M and SR_IMS. GADC may suffer from model mismatch due to the Gaussian assumption and IMS may have suboptimum threshold value due to the inaccuracy of the pdf estimation when processing mammogram data. Additionally, HOLSW is said to be superior to several micro-calcification detectors.

TP and FPI are employed as the metrics. The means of TP and FPI represent the average performance of each method, and their standard deviations are used as a measure of the robustness of each method when applied to different types of images. A better method is identified to be one with higher mean TP value but lower mean FPI value as well as lower TP and FPI standard deviations.

Since HOLSW requires the knowledge of the number of lesions, which is generally not available in real-world applications, the lesion number is adjusted manually, such that the TPs of HOLSW and SR_IMS for each image are the same, and then FPI is employed as a criterion for their performance comparison.

From Table 2, it can be seen that 2SR-GBAD-M and SR_IMS achieve superior performance than the classical methods, GADC and IMS, both in true positive detection and in false positive reduction. HOLSW can attain the similar true positive detection performance to 2SR-GBAD-M and SR_IMS, but it is worse than the two SR noise-enhanced detectors in terms of FPI reduction. 2SR-GBAD-M and SR_IMS have similar detection results, (actually SR_IMS performs a little better) but SR_IMS yields more satisfactory results in terms of FPI reduction. This is because 2SR-GBAD-M updates the threshold based on the Gaussian assumption, and is therefore affected by the model mismatch.

It should be emphasized that the detection performance of the detectors may be further improved if image enhancement techniques are employed before detection and post-processing methods, such as pattern classifiers embedded with other lesion features, are used after the detection procedure.

In summary, automatic detection techniques for micro-calcifications are very important for breast cancer diagnosis and treatment. Therefore, it is imperative that the detection techniques be developed that detect micro-calcifications accurately. The experiments described herein show the development of a lesion detection approach based on SR noise for enhancing the Gaussian assumption-based detectors which suffer from model mismatch, and furthermore show a more general SR noise-based detection enhancement framework. Comparative performance evaluation was carried out via experiments between the presented SR noise-based detection enhancement schemes and several detection and classification techniques with three types of representative abnormal mammograms. The results show that the presented algorithm and the framework resulted in highly encouraging performance in terms of flexibility, detection efficiency and system robustness, which demonstrates the SR noise's capability of enhancing the suboptimal detectors and supports its real-world CAD application.

There are many other proposed embodiments of the present invention. Optimizing the SR noise-based technique with memory described herein will be very useful to further improve the efficiency and robustness of the SR noise-based detection enhancement scheme, by determining the optimum weights for two-peak SR noises. Extension of the SR noise-based technique to enhancing fixed multiple threshold detectors is also contemplated. The performance of SR enhanced variable detectors has been shown to be superior than the fixed ones, where both the SR noise and the critical function can be jointly designed to enhance detection. So SR noise-based detectors incorporating variable critical function are likely to be promising. In the experiments discussed herein, the case where signal and background noise are all independently distributed is considered. Additional embodiments covering the correlated signal and noise case may further improve the detection performance. In addition, the application of the detection schemes developed and described herein to other two types of mammogram lesions, i.e., mass and spiculated lesions, and even other medical images, is contemplated. Finally, the SR noise-enhanced scheme may also be useful in color images, which could be an excellent extension of embodiments of the present invention to more real world applications.

The following Examples described below similarly relate to object detection based on SR noise. However, breast cancer is just one type of object the novel methods can handle. The described methods are directed, in part, to finding an object (such as lesions in an image). The two-peak SR noise introduced before is just one type of stochastic resonance noise which can be used to improve the performance of the detectors and classifiers. The methods are designed for general usages.

The SR noise-enhanced detection schemes can improve any algorithms and systems. To implement these schemes, the only knowledge that is needed is the original input data (no matter 1D, 2D, 3D or others) and the output (detection results) of the existing algorithms and systems.

EXAMPLE 6

Scheme to Improve Thresholding-Based Detectors and Classifiers, and a Scheme to Improve General Detectors and Classifiers This Example contains information that has been previously presented herein above, and relates to improving thresholding-based detectors and classifiers. A problem statement is set forth first, followed by a SR noise-based detection scheme, similar to that which is set forth in Example 4, supra.

A binary statistical decision problem is considered. A choice between the following two hypotheses should be made $$\begin{cases} H_0: & p_{\bar{y}}(\bar{y}; H_0) = p_0(\bar{y}) \\ H_1: & p_{\bar{y}}(\bar{y}; H_1) = p_1(\bar{y}) \end{cases} \quad (1)$$

where $\bar{y}$ is an N-dimensional data vector, i.e., $\bar{y} \in R^N$. $p_0(\bar{y})$ and $p_1(\bar{y})$ are the probability density function (pdf) of $\bar{y}$ under $H_0$ (background) and $H_1$ (lesion) hypotheses, respectively. During the decision process, a test is necessary to choose between the two hypotheses, which can be completely characterized by a critical function, or decision function, $\phi(\bar{y})$, $0 \le \phi(\bar{y}) \le 1$, and $$\phi(\bar{y}) = \begin{cases} 1: & T(\bar{y}) > \gamma \\ \beta: & T(\bar{y}) = \gamma \\ 0: & T(\bar{y}) < \gamma \end{cases} \quad (2)$$

where T is the test statistic and a function of $\bar{y}$. $\gamma$ is the threshold, and $0 \le \beta \le 1$ is a suitable number.

The detection performance of this test can be evaluated in terms of probability of detection ($P_D$) and probability of false alarm ($P_F$), $$P_D^{\bar{y}} = \int_{R^N} \phi(\bar{y}) p_1(\bar{y}) d\bar{y} \quad (3)$$

$$P_F^{\bar{y}} = \int_{R^N} \phi(\bar{y}) p_0(\bar{y}) d\bar{y} \quad (4)$$

where $P_D^{\bar{y}}$ and $P_F^{\bar{y}}$ represent the $P_D$ and $P_F$ of the detector, respectively, based on the input $\bar{y}$. Under Neyman-Pearson formulation, a detector is expected to maximize $P_D^{\bar{y}}$ for a given $P_F^{\bar{y}}$. However, due to the model mismatch and the instability of the image or signal, optimal detector is very hard to be obtained in real-world applications. A goal is to improve $P_D^{\bar{y}}$ of the current detector and at the same time maintain or even reduce $P_F^{\bar{y}}$ by introducing SR noise to $\bar{y}$. SR noise can be introduced to the original data in many ways, e.g., addition, multiplication or even in the transform domain. The additive SR noise is used as an example to show the efficiency of the SR noise-enhanced detection scheme. In this scheme, an appropriate SR noise $\bar{n}$ is added to the original data $\bar{y}$, which yields a new data vector $\bar{z}$ $$\bar{z} = \bar{y} + \bar{n} \quad (5)$$

where $\bar{n}$ is either a random vector with probability density function (pdf) $p_{\bar{n}}(.)$ or a non-random signal. To maximize $P_D^{\bar{z}}$ under the constraint that $P_F^{\bar{z}} \le P_F^{\bar{y}}$, the optimum SR noise (other types of SR noise may also be employed) can be expressed as $p_{\bar{n}}^{opt}(\bar{n}) = \lambda \delta(\bar{n} - \bar{n}_1) + (1-\lambda)\delta(\bar{n} - \bar{n}_2)$, where $\lambda$ and $1-\lambda$ are the occurrence probabilities of the suitable N-dimensional vectors $\bar{n}_1$ and $\bar{n}_2$, and $0 \le \lambda \le 1$. So the optimum SR noise includes three parameters, $\bar{n}_1$, $\bar{n}_2$ and $\lambda$, referred to as two-peak SR noise. If detection is carried out in a pixel by pixel manner, N is equal to 1, $\bar{y}$ and $\bar{z}$ reduce to scalars y and z, and SR noise is introduced in the form of z=y+n.

A SR noise-based detection scheme according to an embodiment of the present invention includes one or more of the following steps. This scheme aims at improving the performance of thresholding-based detectors and classifiers using stochastic resonance noise (which can handle more relatively generic cases than the previously discussed scheme), by repeating the following steps in an iterative manner after an initial detection or classification is done.

Initialization: Initial detection.

Step 1: Probability density estimates are obtained under the two hypotheses (as discussed above herein) using the detected positive (e.g., object) and negative (background) pixels. The detection threshold is updated according to the estimated probability density information.

Step 2: The pixels are detected with the updated threshold in Step 1. The resulting detected positive and negative pixels are employed for estimating probability densities under the two hypotheses.

Step 3: The updated threshold in Step 1 and the newly estimated probability densities in Step 2 are used to determine the SR noise (with the method mentioned in Example 2 if the two-peak SR noise is employed).

Step 4: The original image data are modified by adding SR noise to the original pixel intensities.

Step 5: Detection is performed with the detection threshold updated in Step 1 using the modified data from Step 4. If the difference between two successive detection results is smaller than a pre-set threshold, terminate the algorithm else go to Step 1.

To improve the efficiency and robustness of the detection framework, the two-peak SR noise scheme with memory, which yields multi-peak SR noise as discussed herein above, can be used in Step 4 when introducing the two-peak SR noise to the original data.

A SR noise-based detection scheme according to an alternative embodiment of the present invention includes one or more of the following steps. This scheme aims at improving the generic detectors and classifiers using stochastic resonance noise, which can handle even more generic cases as compared with the immediately preceding scheme, by repeating the following steps in an iterative manner after an initial detection or classification is done.

Initialization: Initial detection.

Step 1: Probability density estimates are obtained under the two hypotheses using the detected positive (e.g., object or lesion) and negative (background) pixels.

Step 2: The original detector (corresponding to $\phi$ in (2) in this Example) and the estimated pdfs in Step 1 are employed to find the optimum SR noise by solving the following optimization problem with respect to the SR noise (if the form of the SR noise is not given) or the parameters of the SR noise (if the form of the SR noise is given and only the parameters of the SR noise need to be determined) (based on the method mentioned in Example 2 if the two-peak SR noise is employed).

maximize $P_D^{\bar{z}}$ subject to $P_F^{\bar{z}} \le P_F^{\bar{y}}$ and $0 \le \lambda \le 1$ where the detection is performed on the SR noise-modified data, and where $\bar{y}$ and $\bar{z}$ denote the original and SR noise-modified data, respectively.

Step 3: The SR noise obtained from the optimization procedure in Step 2 is employed to modify the original image data.

Step 4: The original detector is applied to perform detection on the SR noise modified data. If the difference between two successive detection results is smaller than a pre-set threshold, terminate the algorithm else go to Step 1.

To improve the efficiency and robustness of the detection framework, the two-peak SR noise scheme with memory, which yields multi-peak SR noise as discussed herein above, can be used in Step 3 when introducing the two-peak SR noise to the original data.

EXAMPLE 7

Schemes to Improve General Detectors and Classifiers

This Example describes two schemes directed to improving the generic detectors and classifiers using SR noise, each of which uses a different iterative method from those previously referenced and discussed herein above. In both cases, only the information of the pdf of the image background, i.e., the pdf under $H_0$, is needed.

Suppose there are M pixels in an image, represented by $\{y_1, y_2, \ldots, y_i, \ldots, y_M\}$. The prior probability of $y_i$ belonging to $H_0$ is represented by $\pi_0$, i.e., $\pi_0 = P(H_0)$, and $0 \leq \pi_0 \leq 1$. The original image data are modified by SR noise. Suppose the detection results of applying the original detector to the original data are $a = \{a_1, a_2, \ldots, a_i, \ldots, a_M\}$, and the results of applying the original detector to the SR noise-modified data are $b = \{b_1, b_2, \ldots, b_i, \ldots, b_M\}$, where $a_i$, $b_i = 1$ mean that pixel i is detected to belong to $H_1$, and $a_i$, $b_i = 0$ if i is detected to belong to $H_0$. Thus, the probability of pixels being detected to belong to $H_1$ can be expressed in terms of $P_D$ and $P_F$ as follows $$P(a_i=1) = \pi_0 P_F^y + (1-\pi_0) P_D^y \text{ and } P(b_i=1) = \pi_0 P_F^z + (1-\pi_0) P_D^z \quad (6)$$

In the SR noise-enhanced detection scheme, $P_F^z$ is expected to be smaller or equal to $P_F^y$, so from (6) we have $$(1-\pi_0) P_D^z \geq P(b_i=1) - P(a_i=1) + (1-\pi_0) P_D^y \quad (7)$$

It can be seen that $P(b_i=1)$ is proportional to the lower bound of $P_D^z$. As a special case, $P(b_i=1)$ is proportional to $P_D^z$ if $P_F^z$ is equal to $P_F^y$, which is corresponding to the constant false-alarm rate case. Therefore, higher $P_D^z$ could be expected if $P(b_i=1)$ is higher. So the optimum parameters of the SR noise could be obtained by maximizing $P(b_i=1)$. $P(b_i=1)$ can be estimated by dividing the number of detected positives by M, the total number of pixels in an image. According to the "strong law of large number", it can be shown that the estimated $P(b_i=1)$ converges to the true value of $P(b_i=1)$ almost surely. For a specific image with the fixed number of pixels, $P(b_i=1)$ is proportional to the number of detected positive pixels. So the optimum parameters of the SR noise can be found by solving the following optimization problem:

$$\text{maximize number of detected positives subject to } P_F^z \leq P_F^y \text{ and } 0 \leq \lambda \leq 1 \quad (8)$$

The constrained optimization problem posed in (8) can be solved by many existing optimization algorithms with respect to the SR noise (if the form of the SR noise is not given) or the parameters of the SR noise (if the form of the SR noise is given and only the parameters of the SR noise need to be determined). To enhance the robustness and reduce the variation of the SR noise-enhanced detection, the detection result is obtained by performing detection on the SR noise-modified data multiple times and then fusing the detection results. For example, given the parameter of the SR noise, K SR noise-modified images are generated which correspond to different realizations of the SR noise with the same parameter. The resulting K detection results are obtained by applying the original detector to the K SR noise-modified images. The K detection results are fused to one via a detection fusion scheme described later.

It can be seen from the above discussion that only the pdf under $H_0$, i.e., $p_0$, is required for solving the optimization problem (8). Based on the availability of the knowledge of $p_0$, there are two schemes to find the optimum parameters of the SR noise and to improve the detection performance.

As examples of the case where the form of the SR noise is given, the optimization in (8) is with respect to the three parameters, $\bar{n}_1$, $\bar{n}_2$ and $\lambda$, if the two-peak SR noise is employed, and with respect to mean and variance if Gaussian noise is used.

Scheme 1 (Without Prior Knowledge About $p_0$)

Under this scheme, the case where no prior information about the probability density function of the image background is available is considered. This can be a fully automatic SR noise-based detection method.

An aggressive initial detection is carried out, such that high confidence can be had that all the detected negatives belong to $H_0$, although there will be many false alarms. As an example, in the breast cancer detection, usually the number of background pixels is much larger than that of the lesion pixels, so we still have enough background pixels to obtain an accurate estimate of $p_0$. The following SR noise-based detection scheme according to an alternative embodiment of the present invention includes one or more of the following steps is presented.

Initialization: Initial detection (make sure that all the detected negatives belong to background with high possibility). Set the number of detections in the detection fusion procedure to be K. (All the K detections use the same SR noise parameters but different SR noise realizations.) Set the threshold for fusing the K detection results to be Q, where K and Q are positive integers and $Q \leq K$. It should be made sure that in the initial detection, all the detected negative pixels belong to background with high possibility. The performance of generic detectors and classifiers can be improved using stochastic resonance noise, by repeating the following steps in an iterative manner after an initial detection is done:

Step 1: The pdf of the background pixels in the original image, i.e., $p_0$, is estimated from the detected negative (background) pixels.

Step 2: $p_0$ obtained in Step 1 and the original detector are employed to solve the optimization problem posed in (8) with respect to the SR noise (if the form of the stochastic resonance noise is not given) or the parameters of the SR noise (if the form of the stochastic resonance noise is given and we only need to determine the parameters of it).

maximize number of detected positives subject to $P_F^{\bar{z}} \leq P_F^{\bar{y}}$ where $\bar{y}$ and $\bar{z}$ denote the original and stochastic resonance noise-modified data, respectively. $P_F$ denotes the probability of false alarm rate. Many generic optimization algorithms can be used to solve this constrained optimization problem.

During the optimization, the number of the detected positives is obtained from the following detection fusion scheme Original image data is modified by SR noise, and the detection is performed using the original detectors on the SR noise-modified data. The procedure is repeated K times with the same SR noise parameters, which is corresponding to K different realizations of the SR noise-modified images. For each pixel, we record the times of its being decided to belong to object in the K times of detections. The number of detected positives is equal to the number of pixels whose recorded times of being decided to belong to object is larger than or equal to Q.

Step 3: The SR noise obtained from Step 2 are employed to modify the original image data.

Step 4: Detection is performed by applying the original detector to the modified image data using the detection fusion scheme in Step 2, where a pixels called a detected positive if its recorded times of being decided to belong to object is larger than or equal to Q. If the difference between two successive detection results is smaller than a pre-set threshold, terminate the algorithm else go to Step 1.

Scheme 2 (with Prior Knowledge About $p_0$)

Under this scheme, the case where prior information about the probability density function of the image background exists is considered.

Suppose there exists prior knowledge about $p_0$. For example, in the breast cancer detection, knowledge about $p_0$ can be learned from the mammograms without lesions or the ground-truth non-lesion pixels marked by radiologists. In this case, the estimation of $p_0$ for a specific image can be improved by fusing the prior $p_0$ and the estimated $p_0$ of the image under consideration, and thereafter improve the detection performance. There are lots of schemes for fusing pdf, and one example of a SR noise-based detection scheme is shown according to an alternative embodiment of the present invention that includes one or more of the following steps:

Initialization: Initial detection. Set the number of detections in the detection fusion procedure to be K. (All the K detections use the same SR noise parameters but different SR noise realizations.) Set the threshold for fusing the K detection results to be Q, where K and Q are positive integers and Q≤K. The performance of generic detectors and classifiers can be improved using SR noise, by repeating the following steps in an iterative manner after an initial detection is done:

Step 1: The pdf of the background pixels in the original image, i.e., $p_0$, is estimated from the detected negative (background) pixels, denoted by $p_0^{est}$, which is fused with the prior pdf, denoted by $p_0^{prior}$, using the following convex combination:

$$p_0 = \left(1 - \frac{1}{l+1}\right)p_0^{est} + \frac{1}{l+1}p_0^{prior} \qquad (40)$$

where l is the number of iterations, l={1, 2, . . . }. That is, with the iteration proceeding it is assumed that the pdf estimated from the detection result, i.e., $p_0^{est}$, becomes more and more reliable, which is helpful to take into account the specific features of the image data under consideration.

Step 2: $p_0$, obtained in Step 1 and the original detector are employed to solve the optimization problem posed in (8) with respect to the SR noise (if the form of the stochastic resonance noise is not given) or the parameters of the stochastic resonance noise (if the form of the stochastic resonance noise is given and we only need to determine the parameters of it).

maximize number of detected positives
subject to $P_F^{\bar{z}} \le P_F^{\bar{y}}$
where $\bar{y}$ and $\bar{z}$ denote the original and stochastic resonance noise-modified data, respectively. $P_F$ denotes the probability of false alarm rate. Many generic optimization algorithms can be used to solve this constrained optimization problem.

During the optimization, the number of the detected positives, as the value of the objective function to be maximized, is obtained from the following detection fusion scheme:

Original image data is modified by stochastic resonance noise, and the detection is performed using the original detectors on the stochastic resonance noise-modified data. The procedure is repeated K times with the same stochastic resonance noise parameters, which is corresponding to K different realizations of the stochastic resonance noise noise-modified images. For each pixel, we record the times of its being decided to belong to object in the K times of detections. The number of detected positives is equal to the number of pixels whose recorded times of being decided to belong to object is larger than or equal to Q.

Step 3: The SR noise obtained from Step 2 are employed to modify the original image data.

Step 4: Detection is performed by applying the original detector to the modified image data using the detection fusion scheme in Step 2, where a pixels is called a detected positive if its recorded times of being decided to belong to object is larger than or equal to Q. If the difference between two successive detection results is smaller than a pre-set threshold, terminate the algorithm else go to Step 1.

While several embodiments of the invention have been discussed, it will be appreciated by those skilled in the art that various modifications and variations of the present invention are possible. Such modifications do not depart from the spirit and scope of the claimed invention.

What is claimed is:

1. A method of improving the performance of a threshold-based detector or classifier, and increasing the probability of detecting or classifying at least one object in an image, said method comprising the steps of:
   a. obtaining image data by using an imaging system, wherein said image data comprises a first set of positive pixels and negative pixels;
   b. calculating stochastic resonance noise with a processor by determining the stochastic resonance noise probability density function that maximizes the probability of detection while not increasing the probability of false alarm, and calculating the stochastic resonance noise data probability density function from a known probability density function for said image data, wherein the stochastic resonance noise probability density function can have the form of $p_n^{opt}(n)=\lambda\delta(n-n_1)+(1-\lambda)\delta(n-n_2)$, with values $n_1$ and $n_2$ equal to two delta function locations having probabilities of $\lambda$ and $1-\lambda$ respectively, where $n_1$ and $n_2$ denote two discrete vectors, $\lambda$ denotes the probability of occurrence of said two vectors, and n is a randomization of said two discrete vectors added with the probabilities of $\lambda$ and $1-\lambda$, respectively; and
   c. adding said stochastic resonance noise to said image data by using said processor, thereby improving the performance of a threshold-based detector or classifier and increasing the probability of detecting or classifying at least one object in an image.

2. The method of claim 1, further comprising the step of calculating a detection or classification threshold for said threshold-based detector or classifier.

3. The method of claim 2, further comprising obtaining a first set of probability density estimates using the detected positive pixels and negative pixels.

4. The method of claim 3, wherein the step of obtaining said first set of probability density estimates using the detected first set of positive pixels and negative pixels further comprises the step of obtaining said first set of probability density estimates under the following two hypotheses:

$$\begin{cases} H_0: p_{\bar{y}}(\bar{y}; H_0) = p_0(\bar{y}) \\ H_1: p_{\bar{y}}(\bar{y}; H_1) = p_1(\bar{y}). \end{cases}$$

where $\bar{y}$ is an N-dimensional data vector, $\bar{y} \in R^N$, $p_0(\bar{y})$ and $p_1(\bar{y})$ are probability density functions of $\bar{y}$ under $H_0$ representing a negative pixel hypothesis, and under $H_1$ representing a positive pixel hypothesis.

5. The method of claim 4, further comprising the step of updating said detection or classification threshold for said threshold-based detector or classifier according to said first set of probability density estimates.

6. The method of claim 5, further comprising the step of detecting a second set of positive pixels and negative pixels with said updated detection threshold.

7. The method of claim 6, further comprising the step of obtaining a second set of probability density estimates using the detected second set of positive pixels and negative pixels.

8. The method of claim 3, wherein the step of obtaining said second set of probability density estimates using the detected second set of positive pixels and negative pixels further comprises the step of obtaining said second set of probability density estimates under the following two hypotheses:

$$\begin{cases} H_0: p_{\bar{y}}(\bar{y}; H_0) = p_0(\bar{y}) \\ H_1: p_{\bar{y}}(\bar{y}; H_1) = p_1(\bar{y}). \end{cases}$$

where $\bar{y}$ is an N-dimensional data vector, $\bar{y} \in R^N$, $p_0(\bar{y})$ and $p_1(\bar{y})$ are probability density functions of $\bar{y}$ under $H_0$ representing a negative pixel hypothesis, and under $H_1$ representing a positive pixel hypothesis.

9. The method of claim 8, wherein the step of calculating stochastic resonance noise further comprises the step of using said updated detection or classification threshold and said second set of probability density estimates to calculate the stochastic resonance noise.

10. The method of claim 9, further comprising the step of performing the step of detection or classification on the stochastic resonance noise modified image data.

11. The method of claim 10, wherein each of said steps are performed in an iterative manner.

12. The method of claim 10, wherein said steps are repeated in an iterative manner if the difference between two successive detection or classification results is larger than a pre-set threshold value.

13. The method of claim 4, further comprising the step of performing a test to choose between the two hypotheses, which is characterized by a critical function, or decision function, $\phi(\bar{y})$, $0 \leq \phi(\bar{y}) \leq 1$, and $$\phi(\bar{y}) = \begin{cases} 1: & T(\bar{y}) > \gamma \\ \beta: & T(\bar{y}) = \gamma \\ 0: & T(\bar{y}) < \gamma. \end{cases}$$

where T is a test statistic and a function of $\bar{y}$, $\gamma$ is the threshold, and $0 \leq \beta \leq 1$ is a suitable number.

14. The method of claim 13, wherein a detection or classification performance of said test is evaluated in terms of probability of detection ($P_D$) and probability of false alarm ($P_F$), $$P_D^{\bar{y}} = \int_{R^N} \phi(\bar{y}) p_1(\bar{y}) d\bar{y}$$

$$P_F^{\bar{y}} = \int_{R^N} \phi(\bar{y}) p_0(\bar{y}) d\bar{y}.$$

where $P_D^{\bar{y}}$ and $P_F^{\bar{y}}$ represent the $P_D$ and $P_F$ of the threshold-based detector, respectively, based on the input $\bar{y}$.

15. The method of claim 14, wherein said stochastic resonance noise is represented by $\bar{n}$, and is added to the original data data $\bar{y}$, which yields a new data vector $\bar{z}$ as follows $$\bar{z} = \bar{y} + \bar{n}$$

where $\bar{n}$ is either a random vector with probability density function $p_{\bar{n}}(.)$ or a non-random signal.

16. A method of improving the performance of a generic detector or classifier, and increasing the probability of detecting or classifying at least one object in an image, said method comprising the steps of:
 a. obtaining image data by using an imaging system;
 b. calculating optimum stochastic resonance noise with a processor, wherein said optimum stochastic resonance noise comprises two-peak stochastic resonance noise having the following expression $p_{\bar{n}}^{opt}(\bar{n}) = \lambda \delta(\bar{n} - \bar{n}_1) + (1-\lambda) \delta(\bar{n} - \bar{n}_2)$, where $\lambda$ and $1-\lambda$ are occurrence probabilities of the suitable N-dimensional vectors $\bar{n}_1$ and $\bar{n}_2$, and $0 \leq \lambda \leq 1$, and where said optimum stochastic resonance noise includes three parameters, $\bar{n}_1$, $\bar{n}_2$ and $\lambda$; and
 c. adding said optimum stochastic resonance noise to said image data by using said processor, thereby improving the performance of a detector and classifier and increasing the probability of detecting or classifying at least one object in an image.

17. The method of claim 16, wherein said optimum stochastic resonance noise is represented by $\bar{n}$, and is added to the original data data $\bar{y}$, which yields a new data vector $\bar{z}$ as follows $$\bar{z} = \bar{y} + \bar{n}$$

where $\bar{n}$ is either a random vector with probability density function $p_{\bar{n}}(.)$ or a non-random signal.

18. The method of claim 17, further comprising the step of maximizing $P_D^{\bar{z}}$ under the constraint that $P_F^{\bar{z}} \leq P_F^{\bar{y}}$, where $\bar{y}$ and $\bar{z}$ denote the original and stochastic resonance noise-modified data, respectively, and where $P_D$ denotes the probability of detection and $P_F$ denotes probability of a false positive.

19. The method of claim 16, wherein said image data comprises a first set of negative or background pixels, and further comprising the step of:
 a. estimating a probability density function, $p_0$, of background pixels in the original image using said obtained first set of negative or background pixels under the following hypothesis:

$$H_0: p_{\bar{y}}(\bar{y}; H_0) = p_0(\bar{y})$$

where $\bar{y}$ is an N-dimensional data vector, $\bar{y} \in R^N$, $p_0(\bar{y})$ is a probability density function of $\bar{y}$ under $H_0$ representing a negative pixel hypothesis.

20. The method of claim 19, further comprising the step of maximizing a number of detected positive pixels under the constraint that $P_F^{\bar{z}} \leq P_F^{\bar{y}}$, where $\bar{y}$ and $\bar{z}$ denote the original and stochastic resonance noise-modified data, respectively, and where $P_D$ denotes the probability of detection and $P_F$ denotes probability of a false positive.

21. The method of claim 16, further comprising the step of detecting fusion by repeating a performance of the step of detection on the stochastic resonance noise modified image data K times with the same stochastic resonance noise parameters corresponding to K different realizations of said stochastic resonance noise-modified images; and the step of recording the number of times a pixel is detected in said stochastic resonance noise modified image data correlating to said object during said K times, wherein a number of detected positive pixels is equal to the number of pixels whose recorded times of correlating to said object is larger than or equal to Q, where K and Q are positive integers, and Q≤K.

22. The method of claim 16, wherein said image data comprises a first set of negative or background pixels, and further comprising the step of:
   a. estimating a probability density function, $p_0$, of background pixels in the original image from the detected negative or background pixels, denoted by $p_0^{est}$, which is fused with a prior probability density function, denoted by $p_0^{prior}$, using the following convex combination:

$$p_0 = \left(1 - \frac{1}{l+1}\right) p_0^{est} + \frac{1}{l+1} p_0^{prior}.$$

where l is the number of iterations, l={1, 2, . . . }.

23. The method of claim 22, further comprising the step of detecting fusion by repeating a performance of the step of detection on the stochastic resonance noise modified image data K times with the same stochastic resonance noise parameters corresponding to K different realizations of said stochastic resonance noise-modified images; and the step of recording the number of times a pixel is detected in said stochastic resonance noise modified image data correlating to said anomaly during said K times, wherein a number of detected positive pixels is equal to the number of pixels whose recorded times of correlating to said anomaly is larger than or equal to Q, where K and Q are positive integers, and Q≤K.

* * * * *